(12) United States Patent
Muhlestein et al.

(10) Patent No.: US 11,488,109 B2
(45) Date of Patent: Nov. 1, 2022

(54) IDENTIFICATION OF EMPLOYMENT RELATIONSHIPS BETWEEN HEALTHCARE PRACTITIONERS AND HEALTHCARE FACILITIES

(71) Applicant: Milliman Solutions LLC, Seattle, WA (US)

(72) Inventors: David Muhlestein, Salt Lake City, UT (US); Robert Richards, Salt Lake City, UT (US)

(73) Assignee: Milliman Solutions LLC, Seattle, WA (US)

(*) Notice: Subject to any disclaimer, the term of this patent is extended or adjusted under 35 U.S.C. 154(b) by 371 days.

(21) Appl. No.: 16/782,991

(22) Filed: Feb. 5, 2020

(65) Prior Publication Data

US 2021/0158295 A1 May 27, 2021

Related U.S. Application Data

(60) Provisional application No. 62/939,349, filed on Nov. 22, 2019.

(51) Int. Cl.
*G16H 40/20* (2018.01)
*G06Q 10/10* (2012.01)
(Continued)

(52) U.S. Cl.
CPC ........... *G06Q 10/105* (2013.01); *G06F 16/24* (2019.01); *G06F 16/284* (2019.01);
(Continued)

(58) Field of Classification Search
CPC ................. G06Q 10/105; G06Q 30/04; G06Q 10/06398; G06Q 50/265; G06Q 40/12;
(Continued)

(56) References Cited

U.S. PATENT DOCUMENTS 8,214,232 B2 * 7/2012 Tyler ...................... G06Q 10/10
705/2
8,566,117 B1 10/2013 Troutt et al.
(Continued)

OTHER PUBLICATIONS

Madison et al., Hospital-physician affiliations and patient treatments, expenditures, and outcomes, Health Service Research, 39(2), 257(22), Apr. 2004, 14 pages (Year: 2004).*
(Continued)

*Primary Examiner* — Jason S Tiedeman
(74) *Attorney, Agent, or Firm* — Terrence J. Edwards; TechLaw Ventures, PLLC

(57) ABSTRACT

Systems, methods, and devices for identifying and quantifying an employment relationship between a practitioner and a facility. A method includes identifying carrier claims processed by a practitioner for procedures performed through a facility and matching the carrier claims to the facility to generate matched claims. The method includes calculating a percentage of outpatient claims based on a percentage of office claims performed by the practitioner that did not occur at the facility. The method includes calculating a level of confidence that the practitioner is employed by the facility based on the matched claims and the percentage of outpatient claims.

33 Claims, 8 Drawing Sheets

(51) Int. Cl.

| | | |
|---|---|---|
| *G06F 16/24* | (2019.01) | |
| *G16H 10/60* | (2018.01) | |
| *G16H 70/20* | (2018.01) | |
| *G06F 16/90* | (2019.01) | |
| *G06F 16/28* | (2019.01) | |
| *G06Q 40/00* | (2012.01) | |
| *G06Q 30/00* | (2012.01) | |
| *G16H 50/70* | (2018.01) | |
| *G06Q 10/06* | (2012.01) | |
| *G06Q 50/26* | (2012.01) | |
| *G16H 40/00* | (2018.01) | |
| *G06F 21/60* | (2013.01) | |
| *G06F 21/62* | (2013.01) | |
| *G06Q 30/04* | (2012.01) | |
| *G06Q 40/08* | (2012.01) | |

(52) U.S. Cl.
CPC ............ *G06F 16/288* (2019.01); *G06F 16/90* (2019.01); *G06F 21/602* (2013.01); *G06F 21/6245* (2013.01); *G06Q 10/06398* (2013.01); *G06Q 10/10* (2013.01); *G06Q 30/0185* (2013.01); *G06Q 30/04* (2013.01); *G06Q 40/12* (2013.12); *G06Q 50/265* (2013.01); *G16H 10/60* (2018.01); *G16H 40/00* (2018.01); *G16H 40/20* (2018.01); *G16H 50/70* (2018.01); *G16H 70/20* (2018.01); *G06Q 40/08* (2013.01)

(58) Field of Classification Search
CPC .... G06Q 30/0185; G06Q 10/10; G06Q 40/08; G06F 21/602; G06F 21/6245; G06F 16/284; G06F 16/288; G06F 16/90; G06F 16/24; G16H 40/00; G16H 50/70; G16H 40/20; G16H 10/60; G16H 70/20
USPC .................................................. 705/2, 3, 4
See application file for complete search history.

(56) References Cited

U.S. PATENT DOCUMENTS

| | | | | |
|---|---|---|---|---|
| 10,535,430 | B1* | 1/2020 | Fischer | G16H 10/60 |
| 10,628,834 | B1* | 4/2020 | Agarwal | G06Q 30/0185 |
| 10,867,361 | B1* | 12/2020 | Cave | G16H 40/20 |
| 10,991,457 | B1* | 4/2021 | Hallemeier | G16H 40/20 |
| 11,145,419 | B1* | 10/2021 | Shukla | G06F 16/242 |
| 2003/0083903 | A1* | 5/2003 | Myers | G06Q 30/04 705/2 |
| 2005/0091080 | A1* | 4/2005 | Biats, Jr. | G06Q 40/08 705/2 |
| 2010/0114607 | A1* | 5/2010 | Kress | G16H 40/20 705/3 |
| 2010/0228564 | A1* | 9/2010 | Kharraz Tavakol | G06Q 30/018 705/2 |
| 2011/0022433 | A1* | 1/2011 | Nielsen | G06Q 10/0633 705/7.27 |
| 2011/0125531 | A1* | 5/2011 | Seare | G06Q 40/00 705/3 |
| 2013/0073313 | A1* | 3/2013 | Christakis | G06Q 30/00 705/2 |
| 2013/0110533 | A1 | 5/2013 | Paul et al. | |
| 2014/0278479 | A1* | 9/2014 | Wang | G06Q 10/10 705/2 |
| 2015/0046181 | A1* | 2/2015 | Adjaoute | G06N 5/04 705/2 |
| 2015/0278462 | A1* | 10/2015 | Smoley | G06Q 40/08 705/2 |
| 2016/0019357 | A1* | 1/2016 | Marzula | G06Q 10/10 705/2 |
| 2016/0034648 | A1* | 2/2016 | Mohlenbrock | G16H 40/20 705/3 |
| 2016/0063211 | A1* | 3/2016 | Chen | G16H 50/50 705/3 |
| 2016/0132646 | A1* | 5/2016 | Jones | G06Q 40/08 705/2 |
| 2016/0188819 | A1* | 6/2016 | Subramanian | G06Q 30/018 705/4 |
| 2016/0210427 | A1* | 7/2016 | Mynhier | G16H 10/60 |
| 2017/0017760 | A1* | 1/2017 | Freese | G06F 16/24578 |
| 2018/0240195 | A1* | 8/2018 | Bogle | G16H 40/20 |
| 2019/0355036 | A1* | 11/2019 | Ketchel, III | G06Q 30/0239 |
| 2019/0385126 | A1* | 12/2019 | Morrow | G06Q 40/08 |
| 2020/0020037 | A1* | 1/2020 | Idrobo | G06Q 40/08 |
| 2020/0043579 | A1* | 2/2020 | McEwing | G16H 10/60 |
| 2020/0272740 | A1* | 8/2020 | Obee | G06F 21/577 |
| 2020/0411181 | A1* | 12/2020 | Agnello | G16H 40/67 |
| 2021/0103939 | A1* | 4/2021 | McLean | G16H 40/20 |
| 2021/0133605 | A1* | 5/2021 | Greene | G06N 20/00 |
| 2021/0141834 | A1* | 5/2021 | Mac Manus | G16H 40/20 |
| 2021/0158452 | A1 | 5/2021 | Muhlestein et al. | |
| 2021/0158911 | A1 | 5/2021 | Richards et al. | |
| 2021/0158912 | A1 | 5/2021 | Richards et al. | |
| 2021/0158913 | A1 | 5/2021 | Richards et al. | |
| 2021/0158942 | A1 | 5/2021 | Richards et al. | |
| 2021/0158943 | A1 | 5/2021 | Richards et al. | |
| 2021/0158944 | A1 | 5/2021 | Richards et al. | |
| 2021/0158945 | A1 | 5/2021 | Richards et al. | |

OTHER PUBLICATIONS

Barnett et al., Mapping Phsician Networks with Self-Reported and Administrative data, HSR: Health Services Research 46:5 (Oct. 2011), pp. 1592-1609 (Year: 2011).*

Bynum et al. (Assigning Ambulatory Patients and Their Physicians to Hospitals: A Method for Obtaining Population-Based Provider Performance Measurements, HSR: Health Services Research 42:1, Part I (Feb. 2007), pp. 45-60 (Year: 2007).*

* cited by examiner

US 11,488,109 B2

IDENTIFICATION OF EMPLOYMENT RELATIONSHIPS BETWEEN HEALTHCARE PRACTITIONERS AND HEALTHCARE FACILITIES

CROSS-REFERENCE TO RELATED APPLICATION

This application claims the benefit of U.S. Provisional Patent Application No. 62/939,349, filed Nov. 22, 2019, titled "IDENTIFICATION OF EMPLOYMENT RELATIONSHIPS BETWEEN HEALTHCARE PRACTITIONERS AND HEALTHCARE FACILITIES," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure relates generally to the analysis of healthcare systems and particularly to identifying relationships between healthcare entities.

BACKGROUND

The healthcare industry is extraordinarily complex. Specifically, in the United States, relationships between healthcare practitioners, clinics, facilities, groups, and systems are complex and interwoven such that it can be challenging to identify relationships between different entities. One practitioner may see patients that are part of different systems, health insurance networks, or groups. Further, the practitioner may be associated with more than one facility or clinic. The interwoven relationships between healthcare entities makes it challenging to determine if a certain practitioner is associated with or employed by a certain facility, clinic, group, or system. Additionally, other relationships between practitioners, facilities, clinics, groups, and systems throughout the healthcare industry are difficult to identify and quantify.

In some instances, it is necessary or beneficial to understand the relationships between healthcare entities. For example, a health insurance provider seeking to create an in-network selection of providers may need to know which practitioners are associated with which facilities, clinics, groups, or systems. Further for example, a manufacturer or seller of medical devices or pharmaceuticals may benefit from understanding the business relationships between practitioners, facilities, clinics, groups, and systems. In some instances, for example, the manufacturer or seller may sell a medical device or pharmaceutical to a single group, and this would in turn lead to distribution of that medical device or pharmaceutical to hundreds of practitioners associated with the group. These relationships between healthcare entities are nearly impossible to identify or quantify.

In light of the foregoing, disclosed herein are systems, methods, and devices for identifying relationships between healthcare entities.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Figure 1:
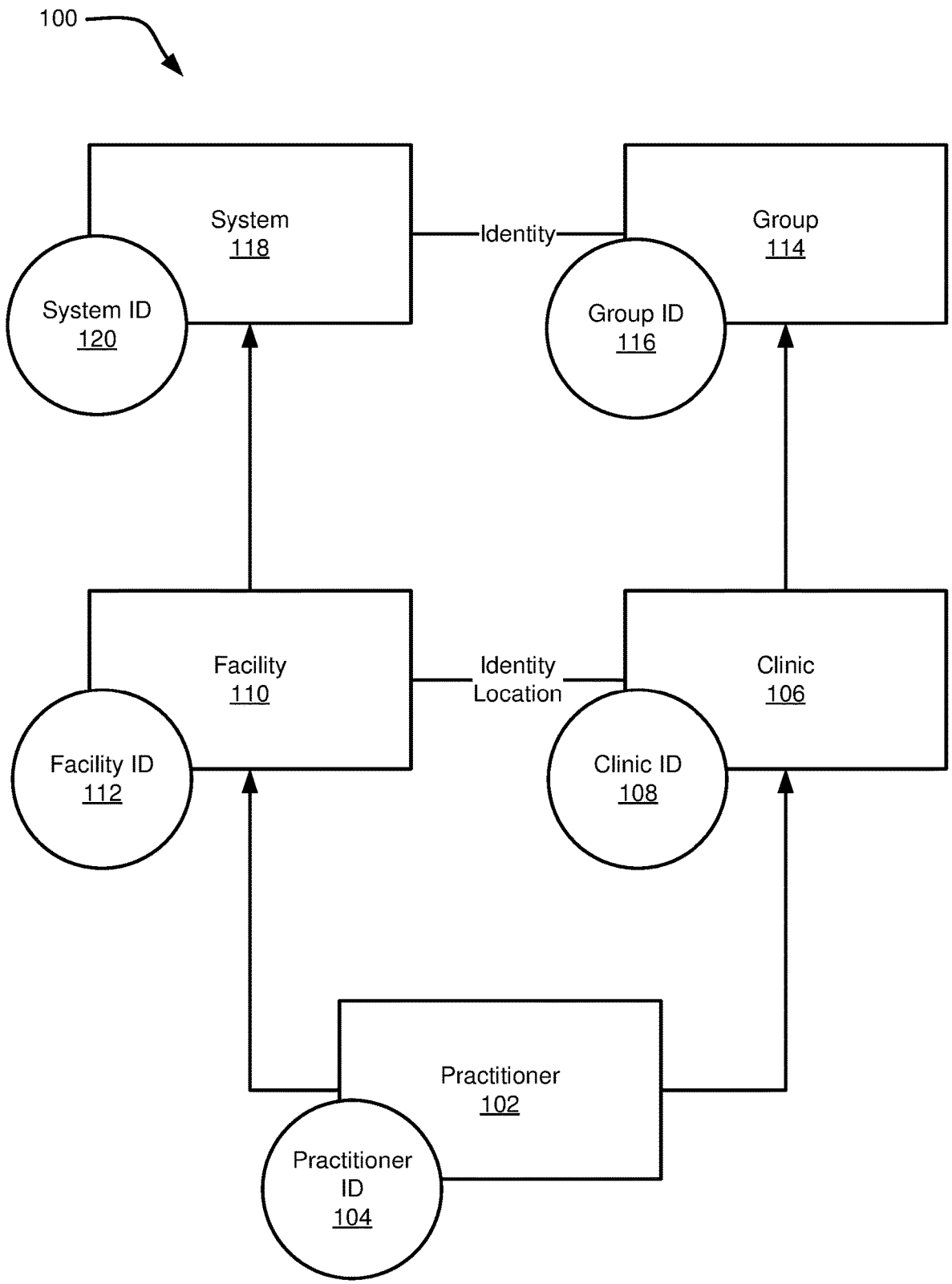
FIG. 1 is a schematic diagram of a framework outlining affiliations between healthcare entities.

Disclosed herein are systems, methods, and devices for identifying and quantifying relationships between healthcare entities. In an embodiment, an employment relationship between a facility and a healthcare practitioner is identified and quantified based on the practitioner's procedures and facility claims.

Current understanding of the healthcare industry in the United States is extremely fragmented. In some instances, it is difficult or impossible to identify systems of care including financial, employment, and enrollment relationships between healthcare entities. The healthcare industry uses multiple data sources for storing billing, procedure, and facility records. There is no one data source that is ideal or reliable for identifying the numerous relationships between healthcare entities.

Embodiments of the disclosure begin at the level of individual practitioner billing and procedure codes and builds from there to identify and quantify relationships between other healthcare entities. By tracking the relationships of individual practitioners to higher level entities, the connections between practitioners and multiple other entities can be identified. This is an improved and more streamlined method when compared with viewing all organizations as discrete, mutually exclusive sets of practitioners.

Embodiments of the disclosure leverage multiple data sources to precisely and completely describe relationships between healthcare entities. Relationships between practitioners and other healthcare entities cannot be viewed as binary. There are multiple types of affiliations between healthcare entities, and each affiliation may be characterized in terms of its strength. An affiliation reported as merely binary (i.e. yes/no, exists/does not exist, and so forth) masks important information.

Embodiments of the disclosure interpret affiliation metrics based on an individualized perspective. For example, a physician's affiliation with a hospital has two perspectives: the physician's perspective and the hospital's perspective. The physician may view the hospital as a necessary portion of the practice that enables the physician to perform certain procedures. The hospital may view the physician as one of many, and the physician's procedures performed at the hospital may represent a very small portion of all procedures performed at the hospital. Understanding affiliations from both perspectives is more informative than viewing the affiliations from only one perspective.

Embodiments of the disclosure describe affiliations in terms of real-world activities that link practitioners to other healthcare entities. This can be performed by assessing disparate data sources in terms of real-world actions or relationships. Some actions, such as referrals or billing of office claims, may come naturally from a single data source. Other actions, such as geographic practice locations and clinic ownership, require synthesis of multiple data sources. The goal is not merely to represent the data sources, but to leverage the data sources to represent the real world. This results in new metrics and relationships that did not exist before. In embodiments of the disclosure, raw data is manipulated to identify real-world relationships that could not previously be identified or quantified.

Embodiments of the disclosure state affiliations between healthcare entities through action. For example, rather than querying practitioners and other healthcare entities about how they believe they are affiliated, it is more accurate to assess actual behaviors that illuminate real-world relationships free from spin, bias, ignorance, misunderstanding, or self-reported outcomes.

Before the structures, systems, and methods for identifying relationships between healthcare entities are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates a framework 100 that outlines affiliations between healthcare entities. The framework 100 is built from the ground up and begins with the practitioner 102. The practitioner may be affiliated with facilities 110 and/or clinics 106. A facility 110 may be affiliated with a system 118. A clinic 106 may be affiliated with a group 114. There may be affiliations between systems 118 and groups 114 and between facilities 110 and clinics 106.

In an embodiment of the framework 100, a distinction is drawn between systems 118 that may own facilities 130, and groups 114 that may own clinics 106. This distinction is made for illustrative purposes and to increase the accuracy of conclusions drawn from assessing healthcare affiliations. In some instances, this distinction does not exist in the real world, and systems 118 and groups 114 functionally operate as the same entities. This serves as justification for the ground-up approach that permits individual practitioner behaviors to be leveraged to describe the relationships of higher-level entities with one another.

The practitioner 102 is a healthcare practitioner such as a physician (Doctor of Medicine), physician assistant, nurse practitioner, podiatrist, dentist, chiropractor, psychologist, optometrist, nurse midwife, clinical social worker, and so forth. The practitioner 102 may be a single person licensed to provide healthcare advice or guidance, perform procedures, prescribe medications, and so forth. The practitioner 102 may be a solo practitioner, may be associated with a group of other practitioners 102 in a clinic 106 or other group setting, may be employed by a facility 110 such as a hospital, may be employed as an in-house practitioner, and so forth. In some instances, it can be beneficial to identify and quantify the practitioner's 102 relationships with other entities such as clinic 106, facilities 130, groups 114, and systems 118.

The practitioner 102 may be associated with a practitioner ID 104. In some embodiments, the practitioner ID is an individual NPI (National Provider Identifier). In the United States, an individual National Provider Identifier (NPI) is a Health Insurance Portability and Accountability Act (HIPAA) administrative standard. An individual NPI is a unique identification number for covered healthcare providers. In the United States, covered healthcare providers, health plans, and healthcare clearinghouses are directed to use NPIs in administrative and financial transactions. It should be appreciated that the practitioner 104 may be associated with any unique identifier and does not need to be associated with a National Provider Identifier. The use of some other unique identifier does not depart from the scope of the disclosure. The practitioner ID 104 is a unique code associated with the practitioner 102. It should be appreciated that the practitioner ID 104 is any unique code associated with the practitioner 102 and can include other codes without departing from the scope of the disclosure.

The clinic 106 is a group of practitioners, a single practitioner, or some other entity that is primarily focused on the care of outpatients. The clinic 106 may be an outpatient clinic, an ambulatory care clinic, a physical therapy clinic, a specialist clinic, an urgent care clinic, an employer-funded in-house healthcare clinic, and so forth. The clinic 106 may be a group of practitioners that practice together at the same physical location or at different physical locations. The clinic 106 may include one or more practitioners 102 that practice telehealth care over the phone, over video communications, or by some other form of communication. The clinic 106 may be privately operated or publicly managed and funded. The clinic 106 may be suited for covering primary healthcare needs or specialized outpatient healthcare needs for populations of communities, in contrast with larger hospitals that offer specialized treatments and admit inpatients for overnight stays. The clinic 106 is not limited to only providing outpatient care.

The clinic 106 may be associated with an clinic ID 108. In some embodiments, the clinic ID 108 is an organization NPI (National Provider Identifier). In the United States, an organization National Provider Identifier (NPI) is a Health Insurance Portability and Accountability Act (HIPAA) administrative standard. An organization NPI is a unique identification number for covered healthcare clinics. The clinic ID 108 is a unique code associated with the clinic 106. If the clinic 106 has multiple geographic locations, then each of the multiple geographic locations for the clinic 106 may have a unique clinic ID 108. In some instances, two or more locations for the same clinic 106 share a clinic ID 108. It should be appreciated that the clinic 106 may be associated with any unique identifier and does not need to be associated with an organization NPI. The use of some other unique identifier does not depart from the scope of the disclosure.

The facility 110 is a physical or virtual healthcare location where an individual can receive care from a practitioner 102. The facility 110 may include hospitals, ambulatory surgical centers, birth centers, blood banks, dialysis centers, hospice centers, imaging and radiology centers, mental health and addiction treatment centers, nursing homes, orthopedic and other rehabilitation centers, telehealth systems, and so forth. In some implementations, it is not necessary to provide a formal definition for a facility 110 versus a clinic 106, and this distinction can be drawn based on the factual circumstances of various healthcare entities.

In an example embodiment, the facility 110 is linked to a facility ID 112. In some embodiments, the facility ID 112 is a Centers for Medicare and Medicaid Services (CMS) Certification Number, which is referred to as a CCN. In the United States, the CCN is the facility's 110 unique identification code that is linked to the facility's 110 provider agreement for Medicare billing. In some instances, the CCN is referred to as the facility's 110 "provider number." The facility ID 112 is used for submitting and reviewing the facility's 110 cost reports. It should be appreciated that the facility 110 may be associated with any unique identifier and does not need to be associated with a CCN. The use of some other unique identifier does not depart from the scope of this disclosure.

The group 114 is a healthcare entity that owns one or more clinics 106. The group 114 may alternatively be referred to as a "provider group." In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

The group 114 may be associated with a group ID 116. In some embodiments, the group ID 116 is a PECOS Associate Control identification (PAC ID). The PECOS is a system used in the United States and enables practitioners and other healthcare facilities to register with the Centers for Medicare and Medicare Services. PECOS is the Provider, Enrollment, Chain, and Ownership System. The system 118 may further be associated with the group ID 116. In some cases, a group 114 and a system 118 are the same entity and are associated with the same group ID 116. In some cases, a group 114 and a system 118 are separate entities to the degree that the group 114 is associated with its own group ID 116 and the system 118 is associated with its own system ID 120.

The system 118 is a healthcare entity that owns one or more facilities 110. In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

There are numerous metrics that can be calculated based on the relationships between practitioners 102, clinics 106, facilities 110, groups 114, and systems 118. In some cases, the metrics are determined based on claims billed by any of the entities described in FIG. 1. Some basic affiliation metrics that can be calculated include practitioner billing metrics, clinic billing metrics, practitioner enrollment metrics, clinic enrollment metrics, practitioner-group billing metrics, group billing metrics, practitioner-facility procedure volume metrics, facility procedure volume metrics, practitioner-facility employment metrics, facility-clinic distance metrics, and others. The practitioner billing metric is the proportion of a practitioner's total office claims billed to a certain clinic associated with a specific clinic ID 108. The clinic billing metric is the proportion of total office claims billed under a clinic performed by a given practitioner. The practitioner enrollment metric is the clinics at which a practitioner is enrolled in the PECOS. The clinic enrollment is the practitioner(s) enrolled in the PECOS under a clinic. The practitioner-group billing is the proportion of the practitioner's office claims billed under any of the group's clinics. The group billing is the proportion of all office claims billed under any of the group's clinics that were performed by a specific practitioner. The practitioner-facility procedure volume is the proportion of a practitioner's total procedure claims performed at each facility. The facility-procedure volume is the proportion of the procedures performed at the facility performed by each practitioner. The practitioner-facility employment is the level of confidence that the practitioner is employed by a given facility. The facility or clinic distance is the distance between a clinic and a facility in miles or some other distance measurement.

Figure 2:
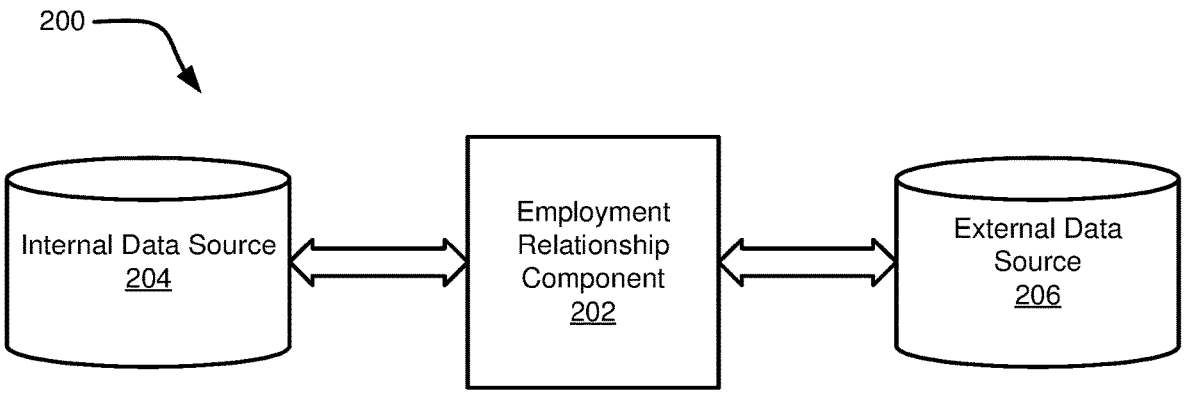
FIG. 2 is a schematic diagram of a system for data communication between an employment relationship component and internal and external data sources.

FIG. 2 is a schematic diagram of a system 200 for data communication between an employment relationship component 202 and internal and external data sources. The employment relationship component 202 identifies and quantifies employment relationships between practitioners and facilities based on real-world claim data. The employment relationship component 202 performs these calculations based on real-world claim data that can be stored in a combination of internal and external data sources. The employment relationship component 202 may communicate with one or more of an internal data source 204 and an external data source 206.

In an embodiment, the employment relationship component 202 communicates directly with an external data source 206 that is managed or owned by a third-party entity. In an embodiment, the external data source 206 is owned and managed by the Medicare system operated by the United States government. In an embodiment, the external data source 206 is a relational database, and the employment relationship component 202 communicates with the relational database by way of an Application Program Interface (API). In an embodiment, the external data source 206 is an encrypted hard-drive that has been shared with the employment relationship component 202. In an embodiment, the external data source 206 is a virtual data center, and the employment relationship component 202 access the data on a virtual server after signing in or undergoing some other authentication step.

In an embodiment, the employment relationship component 202 communicates with an internal data source 204 that is not managed by some other third-party entity. The internal data source 204 may include a file that has been downloaded or otherwise received from some third-party entity, such as the Medicare system. After the file has been downloaded, the file can be managed and manipulated by the employment relationship component 202. The internal data source 204 may include an encrypted hard-drive that is provided by a third-party, such as the Medicare system.

The employment relationship component 202 may receive and translate information from multiple different sources. In an example implementation, the employment relationship component 202 receives enrollment information from a central data warehouse that may be operated internally or by a third-party. The employment relationship component 202 further receives claims data from a different source, for example via a secure connection to a virtual data store by way of an API, by accessing an encrypted hard drive, or accessing an encrypted file that has been downloaded by way of a network connection.

In an embodiment, the data stored in the internal data source 204 has been "cleaned" or pared down to only include necessary or critical information. This can be beneficial to ensure that the totality of the data is a usable size that can be efficiently queried, analyzed, and manipulated. For example, the raw data retrieved from the external data source 206 may include numerous data fields that are not necessary for identifying an employment relationship between a practitioner and a facility. The unnecessary data may be eliminated, and only the necessary data may be stored on the internal data source 204. In an embodiment, the raw data is cleaned and stored in a relationship database.

In an embodiment, the employment relationship component 202 analyzes information stored in the internal data source 204 and/or the external data source 206 by identifying relationships between individual practitioners 102 and their associated clinics 106 and groups 114. In an example use-case, the employment relationship component 202 identifies that Doctor A is performing work for Clinic B. The employment relationship component 202 then identifies all of the practitioners that associate with Clinic B and assessing the carrier claims billed by those practitioners. The employment relationship component 202 aggregates the claim information for all practitioners in Clinic B and combines the information in an effort to answer specific questions, such as whether a certain practitioner is employed by a facility.

The employment relationship component 202, or some other module in communication with the employment relationship component 202, may create intermediary files or tables within a relational database. The intermediary files or tables may include certain information columns that are pertinent to answer a specific question, such as whether a practitioner is employed by a facility. This can be beneficial to ensure that each intermediary file or table is no bigger than it needs to be to include all necessary information for answering the specific question. This decreases the amount of disc storage and/or Random Access Memory (RAM) needed to analyze the information and calculate the answer to the specific question.

Figure 3:
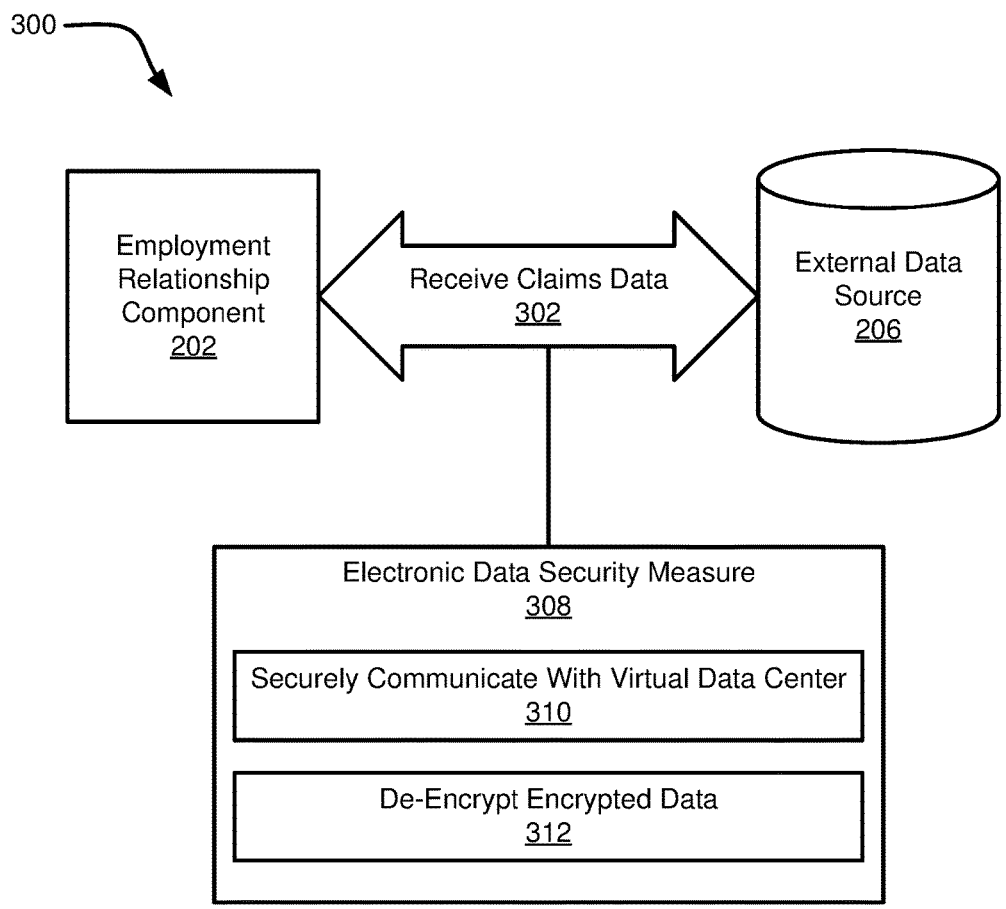
FIG. 3 is a schematic diagram of a system for performing electronic data security measures on data received from an external data source.

FIG. 3 is a schematic diagram of a system 300 for performing electronic data security measures on data received from the external data source 206. The employment relationship component 202 receives claims data (see 302) from an external data source 206. The claims data may include carrier claims, facility claims, and other claims processed by private or public healthcare entities. Claims data includes sensitive information such protected personal information (PPI) and personal identifiable information (PII), and therefore, the claims data must be encrypted or otherwise secured.

In an embodiment, the employment relationship component 202 may receive claims data by securely communicating with a virtual data center (see 310). The virtual data center may be provided by a private or public healthcare entity. In an embodiment, an account may be created for a user associated with the employment relationship component 202, and the user could sign into the virtual data center with the account. The user could then access the data stored in the virtual data center 310 by way of the account. The data may be encrypted or non-encrypted based on the security measures of the virtual data center. In an embodiment, the data may be non-encrypted when viewed by way of a network connection, and the data may be encrypted if downloaded for offline use and manipulation. If the data is downloaded in an encrypted form, then the data must be de-encrypted prior to analysis and manipulation.

In an embodiment, the employment relationship component 202 receives claims data by way of an encrypted hard-drive. The encrypted hard-drive may be provided by the source of the data, such as private or public healthcare entity. In an embodiment, the employment relationship component 202 receives claims data by way of an encrypted file that has been downloaded by way of a network connection. The employment relationship component 202 undergoes an electronic data security measure 308 by de-encrypting the claims data (see 312).

Figure 4:
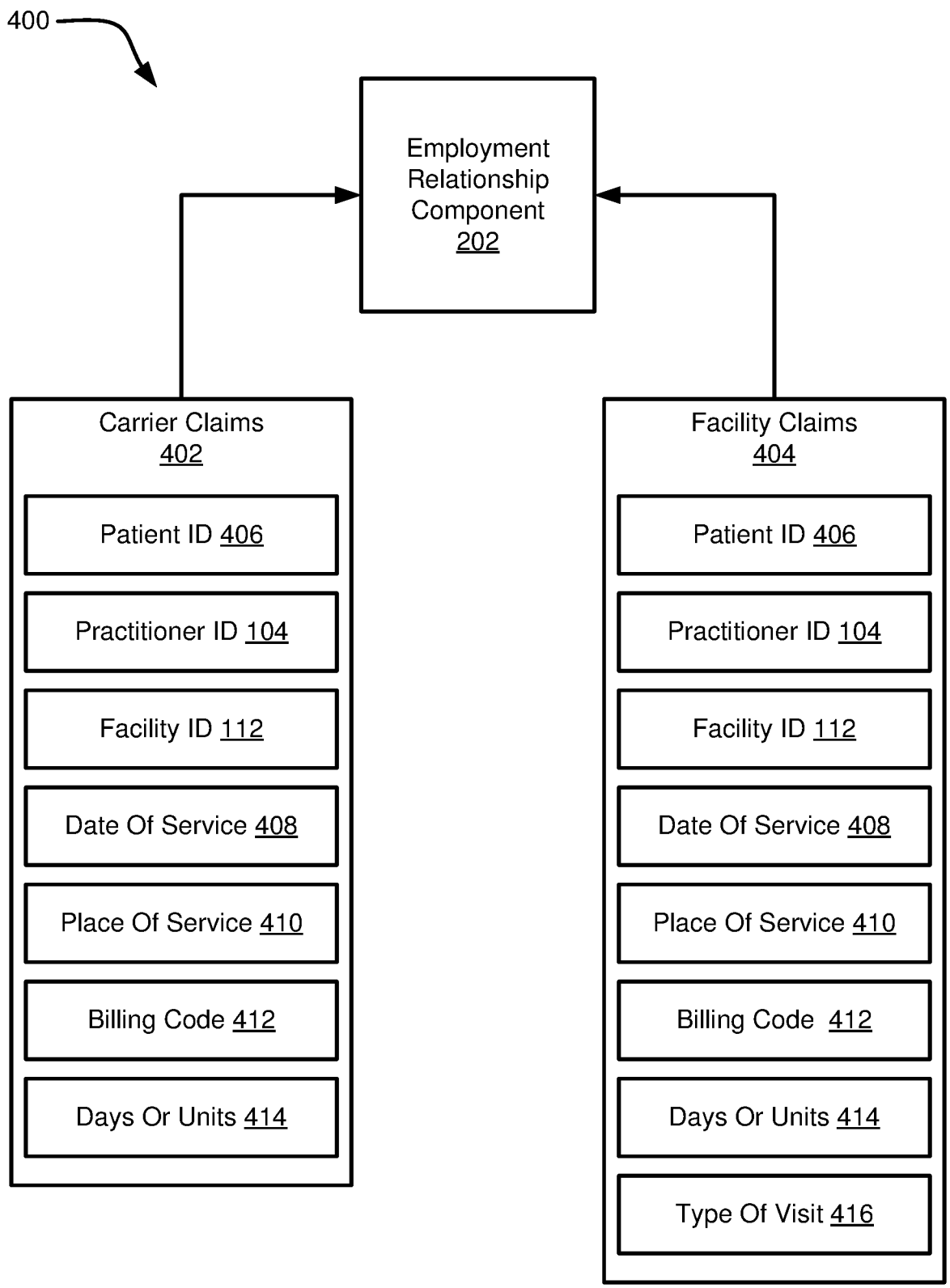
FIG. 4 is a schematic diagram of a data flow for identifying and quantifying an employment relationship between a facility and a practitioner based on carrier claims data and/or facility claims data.

FIG. 4 is a schematic diagram of a data flow 700 for identifying and quantifying an employment relationship between a facility and a practitioner. The employment relationship component 202 receives claim information and determines whether an employment relationship exists between a practitioner and a facility based on the claim information. In an embodiment, the employment relationship component 202 identifies and quantifies a practitioner-facility employment relationship based only on carrier claims 402. In an embodiment, the employment relationship component 202 makes this determination based on carrier claims and facility claims 404.

A carrier claim 402 is a non-institutional medical billing claim submitted by or in behalf of a practitioner 102. The carrier claim 402 may be billed for outpatient or inpatient services. The carrier claims 402 used by the employment relationship component 202 may include carrier claims 402 submitted through the Medicare system implemented in the United States and may additionally include carrier claims for private entities such as private health insurance agencies. If the carrier claims 402 include Medicare claims, then the carrier claim may be submitted on the health insurance claim form CMS-1500 used by the United States Medicare system.

Carrier claims 402 include information about a service provided by a practitioner 102 in an outpatient or inpatient setting. In some instances, only a portion of the information included in the carrier claim 402 is relevant to the analysis of whether an employment relationship exists between a practitioner and a facility. Carrier claims 402 may include a patient identification (ID) 406, which may include a numerical or alphanumerical code assigned to the patient, and may further include the patient's name, address, or other contact information. Carrier claims 402 further include a practitioner ID 104 which may specifically include an individual NPI. The carrier claim 402 may include a facility ID 112, or some other information identifying the name, location, or contact information where the service was performed. The carrier claim 402 includes an indication of the date of service 408 when the service was performed or on what date the service began, if the service extended over multiple days. The carrier claim 402 includes an indication of the place of service 410, and this may be a numerical or alphanumerical code identifying a facility, and may also include a name, address, or other contact information for the facility. The carrier claim 402 includes one or more billing codes 412 identifying the services or procedures that were performed by the practitioner 102. The billing code 412 may include a Healthcare Common Procedure Coding System (HCPCS) code. The carrier claim 402 may further include an indication of the days or units 414 indicating a duration of time the procedure occurred.

The facility claims 404 may include similar information. If the facility claims 404 include Medicare claims, then the facility claims may be submitted on the health insurance claim form UB-40 used by the United States Medicare system. The facility claims 404 may include, for example, the patient ID 406, practitioner ID 104, facility ID 112, date of service 408, place of service 410, billing code 412, days or units 414, and an indication of the type of visit 416. The indication of the type of visit 416 may be a numerical code indicating whether the visit was an emergency, an outpatient visit, an inpatient visit, and so forth.

Carrier claims 402 may include additional information not illustrated in FIG. 4. For example, carrier claims 402 may include an indication of whether the bill is being submitted through a government-funded plan such as Medicare, Medicaid, Tricare, or CHAMPVA, or a private health insurance plan. The carrier claim 402 may include insurance information, such as the insured's ID number, name, address, birth date, policy name, group number, policy number, whether there is an additional health benefit plan, and so forth. The patient ID 406 information may include the patient's name, address, telephone number, and so forth. The carrier claim 402 may include an indication of whether the patient's condition is related to employment, an automobile accident, or some other accident. The date of service 408 information may include an indication of what date the current illness, injury, pregnancy, or other condition began. The date of service 408 may further include other applicable dates. The carrier claim 402 may include information about what dates the patient was unable to work in his or her current occupation, dates of hospitalization related to the current services, charges made to an outside lab in relation to the current services, and so forth. The carrier claim 402 may include information about a referring provider or other source, such as the referring provider's individual NPI. The billing code 412 may include a diagnosis code or an indication of the nature of illness or injury and may further include a CPT or HCPCS code indicating the procedures, services, or supplies used in connection with the billed claim. For each billing code 412 listed in the carrier claim 402, there is also an indication of the date of service, the place of service, the diagnosis pointer, the charges, the days or units, and the rendering provider's practitioner ID 104 for that service, procedure, or supply. The carrier claim 402 may further include a federal tax ID number for the practitioner 102, a patient account number relating to the practitioner's practice, a total charge and the amount paid. The carrier claim 402 additionally includes information on the facility where the service, procedure, or supply was administered to the patient. The information on the facility may include the name, address, contact information, or a clinic ID 108 or facility ID 112 related to the facility.

Facility claims 404 may include additional information not illustrated in FIG. 4. The facility claims 404 may include all of the information listed above with reference to the carrier claims 402. The facility claims 404 may additionally include information on when the patient was admitted to the facility, the condition codes pertaining to why the patient was admitted to the facility, and the dates the patient was in-patient or out-patient at the facility. The facility claim 404 may include numerous practitioner IDs 104 pertaining to each of the numerous practitioners 102 who assisted in the patient's care while the patient was at the facility 110. Each service, procedure, or supply administered to the patient during the patient's stay at the facility 110 may linked to a certain practitioner 102.

Figure 5:
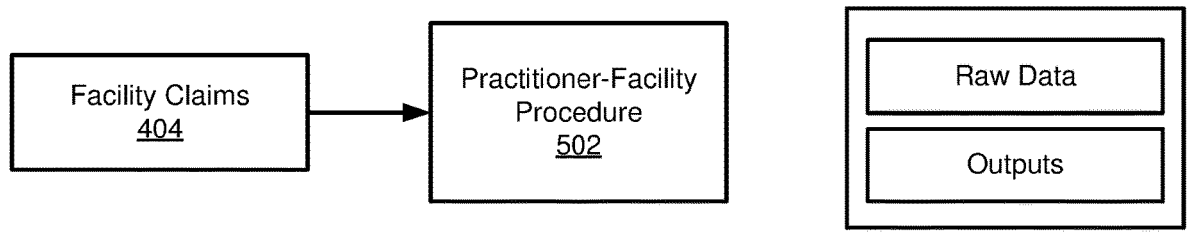
FIG. 5 is a schematic diagram of a data framework for identifying and quantifying practitioner-facility procedure relationships.

FIG. 5 is a schematic diagram of a data flow for identifying and quantifying the practitioner-facility relationship with respect to procedures. The analysis discussed in connection with FIG. 5 can be used to determine at what facilities a practitioner is performing procedures. This is referred to as the practitioner-facility procedures 502 metric.

When a practitioner 102 performs a procedure at a facility, a facility claim 404 is submitted that includes the practitioner's 102 practitioner ID 104, clinic ID 108 for an associated clinic 106, and a CMS Certification Number (facility ID). The facility ID may alternatively be referred to as a CMS provider number. The proportion of procedures performed by a practitioner at a certain facility 110 is quantified based on the relationship in the claims between practitioner IDs and facility IDs. Further, the proportion of the facility's 110 procedure volume that were performed by a certain practitioner 102 is quantified based on the relationship in the claims between practitioner IDs and facility IDs. These procedure volumes provide a link between practitioners 102 and facilities 110 apart from any official ownership or employment relationships.

The raw data input includes all facility claims files such as inpatient, outpatient, hospice, and so forth. The practitioner-facility procedure 502 is determined by identifying the distinct NPIs that participated in each claim. This can be performed for each claim in a given year. Participating NPIs are in the attending, operating, rendering, and other NPI fields. An NPI can appear in more than one of these fields and the duplicates should be handled when calculating the practitioner-facility procedures 502 metric. For each pair including a participating NPI and a facility ID 132, the number of claims represented by the pair is counted. The claim numbers by distinct pair are summed across all claim files. This process may be repeated for each year of available claims data.

The practitioner-facility procedures 502 metrics results in a practitioner facility procedure volume metric and a facility procedure volume metric. The practitioner facility procedure volume metric is the proportion of a practitioner's total procedure claims performed at a certain facility. A practitioner's procedure claim is a claim in which the practitioner participated in the procedure. The facility procedure volume is the proportion of procedures performed at a certain facility by each of one or more practitioners using the certain facility.

Figure 6:
FIG. 6 is a schematic diagram of a data framework for identifying and quantifying practitioner-facility employment relationships.

FIG. 6 is a schematic diagram of a data flow for identifying employment relationships between practitioners and facilities. The analysis discussed in connection with FIG. 6 can be used to determine what facilities directly employ a practitioner. This is referred to as the practitioner-facility employment 504 metric. When a practitioner is directly employed by a facility, the practitioner's billed claims will likely be processed by the facility. In such an instance, the facility might submit a bill including facility charges and practitioner charges, and the practitioner does not send a separate bill. This billing relationship impacts the dynamic between the practitioner and the facility, and further impacts the dynamics between the practitioner and other entities such as healthcare groups, healthcare systems, health insurance agencies, patients, and so forth. Therefore, it can be important to understand whether a practitioner 102 has a direct employment relationship with a facility 110.

In some cases, a practitioner 102 is employed directly by a facility 110. This is distinct from practitioners 102 who practice exclusively at the facility 110. In an embodiment, to determine employment, office-based claims with facility IDs (Centers for Medicare and Medicaid Services (CMS) Certification Numbers) 112 are matched using a multiple step matching process. The proportion of a practitioner's total carrier claims 402 performed in a facility is calculated based on the result of the multiple step matching process.

In some instances, a practitioner 102 is paid less on an office-based claim if there is a facility fee associated with the claim. This occurs because the facility 110 is also billing for the service. The total of the practitioner's 102 fee and the facility 110 fee in these cases is generally higher than the practitioner's 102 fee would be alone at a non-facility setting. Identifying this scenario can lead to concluding that practitioners billing office claims at a facility 110 are employed by the facility 110. When performing this analysis on typical real-world data, the analysis confirms that a majority of practitioners 102 bill all carrier claims 402 or no carrier claims 402 under a facility 110. In an embodiment, practitioners with claims that are all matched to a facility are deemed employed by that facility 110.

The practitioner-facility employment 504 determination can be performed based on a claims analysis file. The claims analysis file is generated based on claims analytics and practitioner affiliations. The claims analytics and practitioner affiliations are identified based on billed claims. In an embodiment, the practitioner-facility employment 504 determination is calculated at least in part based on the result of a multiple step data merging process for matching facility claims 404 (facility IDs) to carrier claims 402. The data merging process occurs by attempting to match unmatched carrier claims 402 from a prior step to practitioners using one or more of the following variables. A possible variable is the patient, service data, and HCPCS (Healthcare Common Procedure Coding System) code. The HCPCS code may alternatively be referred to as a "procedure code" herein. A further possible variable is the patient, service date, and practitioner NPI. A further possible variable is the match based on inpatient location if the carrier claim occurs during a hospitalization and is then matched to that facility. A further possible variable is the service date and the practitioner's most common facility. A further possible variable is the most common facility based on the clinic ID in the carrier claim. A further possible variable is the service date and the practitioner's most common facility. A further possible variable is the service date and the practitioner's most common facility within a two-week range. A further possible variable is the service date and the practitioner's most common facility. A further possible variable is the practitioner's most common provider within two weeks using the previously joined facilities. A further possible variable is the facility that is most closely attached with the clinic ID from the carrier claim.

In an embodiment, the facility claims 404 (facility IDs accessible via PECOS) are matched to carrier claims 402 using the following 10-step merge process. The merge occurs by attempting to match unmatched carrier claims 402 from the prior step to practitioners 102 using the following variables:

i. Patient, service date, and HCPCS code;
ii. Patient, service date, and practitioner's practitioner ID;
iii. Inpatient location if the carrier claim occurs during a hospitalization at the facility;
iv. Service date and practitioner's most common facility;
v. Most common facility based on the clinic ID in the carrier claim;
vi. Service date and the practitioner's most common facility (again);
vii. Service date and the practitioner's most common facility within a two-week time period;
viii. Service date and the practitioner's most common facility (again);
ix. Practitioner's most common provider within two weeks, using the previously joined facilities; and
x. The facility most closely attached to the clinic ID from the carrier claim.

When the data has been merged, a method may further include calculating the percentage of a practitioner's 102 office claims that occurred at a facility 110 by collapsing the practitioner's practitioner ID 104 and the facility's clinic ID 108. In an embodiment, office claims that have a place of service code equal to eleven (office-based claims) or twenty-two (hospital outpatient department claims) are used to determine employment. The proportion of such claims that have place of service code 22 represents the strength of the practitioner's 102 employment relationship with the facility 110. A method may further include collapsing to the clinic 106 or group 114 level and saving a percent of the group's 114 practitioners 102 that are employed by facilities or systems. This can be performed for all years of available claims.

The analysis performed for identifying a practitioner-facility employment 504 relationship can result in a practitioner employment relationship. The practitioner employment metric is a level of confidence that a practitioner is employed by a certain facility.

Groups 114 and clinics 106 can be thought of as "capturing" practitioners 102 who practice at or are employed by a facility 110 or system 118. Through billing capture measures from the facility 110 or system 118 perspective, it can be determined whether the system 118 or facility 110 is working with a handful or large groups 114 of clinics 106, or if the system 118 or facility 110 is working with a larger number of relatively small groups 114 or clinics 106. Further, it can be determined from the group's 114 or clinic's 106 perspective the extent to which the group or clinic captures a system 118.

One goal in calculating the practitioner-facility employment 504 metric is to leverage real-world data sources, such as carrier claims 402 and facility claims 404, to identify an employment relationship present in the real word. The practitioner-facility employment 504 relationship has not previously been identifiable or quantifiable by outside parties prior to the disclosures presented herein. The practitioner-facility employment 504 metric is based on raw data that is accessible and readable to parties outside the relationship itself. This enables raw data to be leveraged and manipulated to create a new metric that identifies and quantifies a real-world employment relationship.

The merge process for matching carrier claims 402 to a facility 110 and/or facility claims 404 is a novel data manipulation process that is performed on a very large set of data. The number of carrier claims 402, facilities 110, and facility claims 404 can be enormous for a singular calendar year. This number of claims is impossible for a single human or group of humans to process, and particularly within the same calendar year of the billed claims. The merge process is a novel set of rules specifying how carrier claims 402 should be matched to a facility 110 and or to facility claims 404.

In an embodiment, the carrier claims 402, the facility IDs 112, and the facility claims 404 are stored in a database. The data (i.e., the combination of the carrier claims 402, the facility IDs 112, and the facility claims 404) is typically retrieved from larger files or data stores and includes superfluous information that is not necessary for identifying and quantifying the practitioner-facility employment 504 relationship. The data is therefore cleaned prior to storage in the database. The data is cleaned such that 10-step matching process can be performed on a manageable sum of data. In an embodiment, the data is equivalent to about 1 terabyte (TB) of data per claim year.

In an embodiment, the cleaned data is linked to a database platform. The database platform is in communication with a user interface (UI) such that the data can be viewed seamlessly. The data can be partitioned within the database based on calendar year, entity, practitioner 102, facility 110, facility ID 112, carrier claim 402, facility claim 404, and so forth. The database platform is built on highly modeled, as opposed to raw, data sources.

In an embodiment, as information stored in the database is changed, the practitioner-facility employment 504 metric is reevaluated. A change to the information stored in the database may reflect that a new facility 110 is added, a new practitioner 102 is added, there is a new relationship between a practitioner and a facility, there are new claims submitted, and so forth. The practitioner-facility employment 504 metric may be reevaluated to determine whether a new employment relationship has been formed, an employment relationship has been discontinued, or an employment relationship has changed. This reevaluation can be performed in real-time as the data as changed and can therefore provide an up-to-date and reliable representation of the real-world relationships between practitioners and facilities. Conducting this analysis by hand (by the human mind) in real-time would be so impractical that it could be considered impossible.

Figure 7:
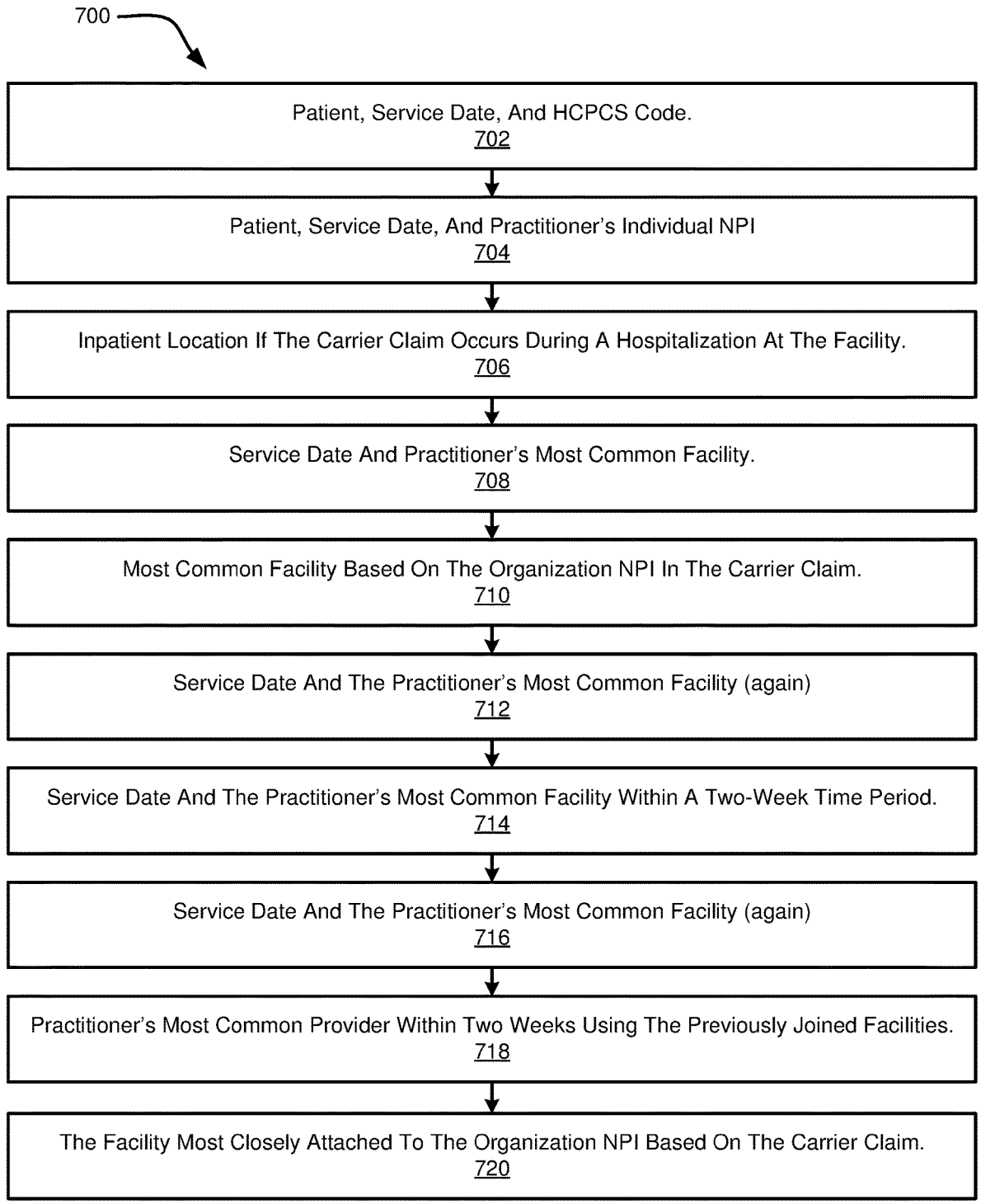
FIG. 7 is a schematic flow chart diagram of a matching process identifying different metrics for matching carrier claims and facility claims.

FIG. 7 is a schematic flow chart diagram of a data flow 700 for matching facility claims 404 and carrier claims 402 to identify and/or quantify an employment relationship between a practitioner 102 and a facility 110. In an embodiment, the facility claims are processed with facility IDs 112 and the practitioner claims are processed with the practitioner's practitioner ID 104. The data flow 700 illustrates the different metrics or variables that are used for the process of matching the facility IDs 112 and practitioner IDs 104 in furtherance of identifying an employment relationship between the practitioner 102 and the facility 110.

In the data flow 700, the first metrics used in the merge process includes the patient, service date, and the HCPCS (Healthcare Common Procedure Coding System) code (see 702). In the United States, HCPCS codes are used for billing Medicare and Medicaid patients. The HCPCS codes are a collection of codes that represent procedures, supplies, products, and services which may be provided to Medicare beneficiaries and to individuals enrolled in private health insurance programs. The data flow 700 continues and the next metrics used in the merge process includes the patient, service data, and the practitioner's practitioner ID 104 (see 704). The data flow 700 continues and the next metric used in the merge process includes the inpatient location if the carrier claim 402 occurs during a hospitalization at the facility 110 (see 706). The next metrics used in the merge process includes the service date and the practitioner's most common facility (see 708). The next metric used in the merge process includes the most common facility for the practitioner based on the clinic ID 108 in the carrier claim 402 (see 710). The next metric used in the merge process is, again, the service date and the practitioner's most common facility (see 712). The next metrics used in the merge process include the service date and the practitioner's most common facility within a two-week time period (see 714). The next metrics used in the merge process include, again, the service date and the practitioner's most common facility (see 716). The next metric used in the merge process includes the practitioner's most common provider within a two-week period using the previously joined facilities (see 718). The next metric used in the merge process is the facility most closely attached to the clinic ID 108 based on the carrier claim 402 (see 720).

Figure 8:
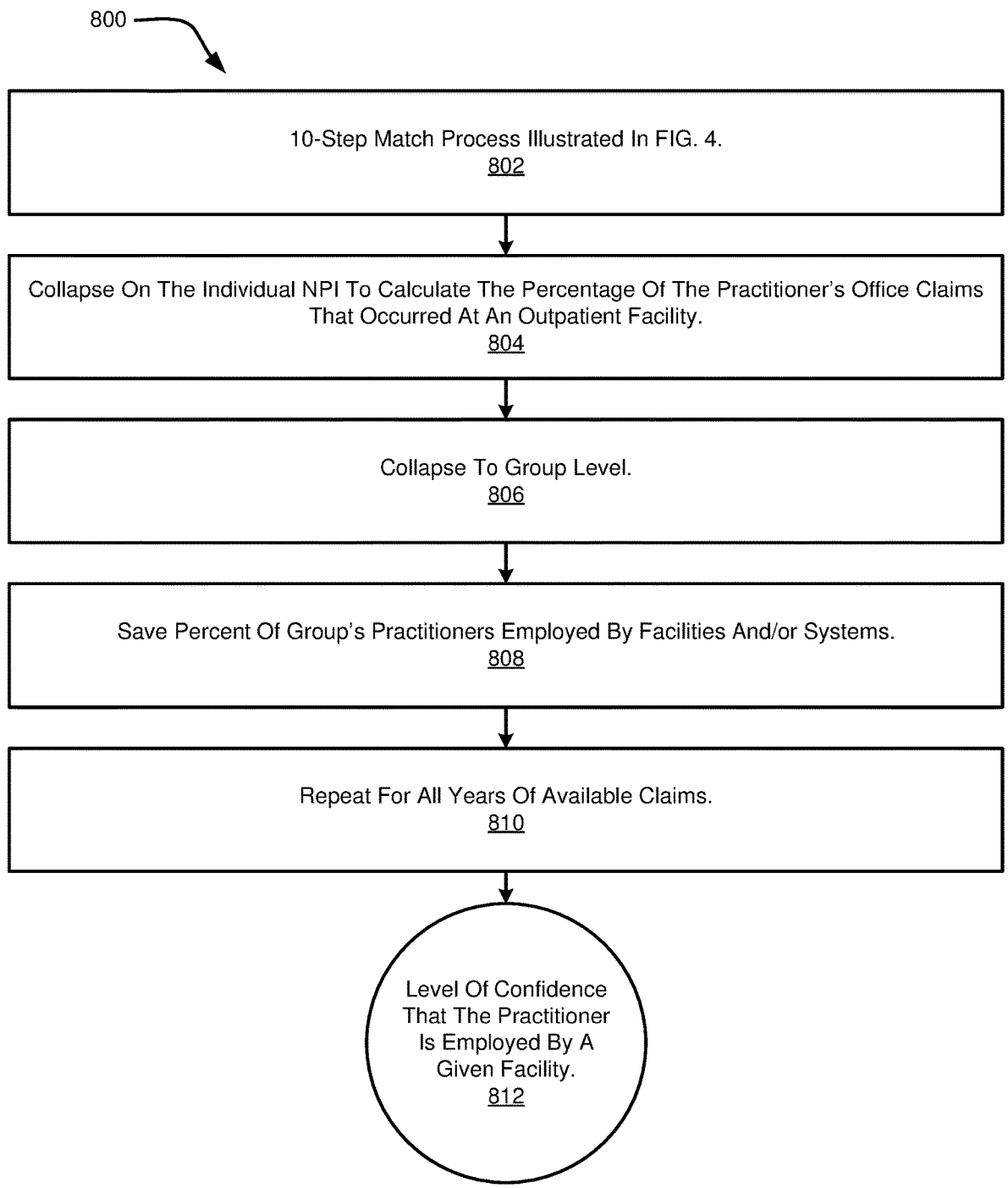
FIG. 8 is a schematic flow chart diagram of a method for calculating a level of confidence that a practitioner is employed by a given facility.

FIG. 8 illustrates a schematic flow chart diagram of a method 800 for merging carrier claims 402 and facility claims 404 to determine the practitioner-facility employment 504 relationship. The method 800 may be performed by a computer system or other suitable calculation device.

The method 800 includes performing at 802 the 10-step match process illustrated in FIG. 4. The 10-step match process includes matching facility IDs to practitioner IDs according to the data flow 700 of various pertinent metrics. The method 800 includes collapsing at 804 on the practitioner ID to calculate the percentage of the practitioner's office claims that occurred at an outpatient facility. The method 800 includes collapsing at 806 to group level. The method 800 includes saving at 808 a percent of the group's practitioners employed by facilities and/or systems. The method 800 includes repeating at 810 all steps 802-808 for all years of available claims. The resulting metric 812 is the level of confidence that the practitioner is employed by a given facility.

In an embodiment, billing capture relationships can be determined by performing one or more of the following steps. A method may include creating a group-system pair based on practitioner IDs billing under the group and performing procedures at the system. The method may include calculating the percent of all the group's office claims that were performed by the system's practicing providers weighted by the procedure affiliation with the system. The method may include calculating the percent of all office claims billed by the system's practitioners that were billed under the group and weighted by procedure affiliation. The method may include saving each of a plurality of group-system pairs and generating a summary file for each system and each group. This may further include calculating summary metrics for the system including the system's capture HHI sum of squared shares of system procedures. This may further include calculating summary metrics for the group that include the group's capture HHI sum of squared shares of the group's procedures. The aforementioned method steps can be performed for all years of available claims.

In an embodiment, it can be beneficial to determine the procedure capture for different healthcare entities. As with billing capture, procedure capture calculates metrics for a system's or facility's capture of a group's or clinic's practitioners' procedures. In an embodiment, a method for determining procedure capture metrics includes one or more of the following steps. The method may include creating a group-system pair based on practitioner IDs billing under the group and performing procedures at the system. The method may include calculating the percent of all procedures performed at the system that were performed by the group's billing providers weighted by their billing affiliation and number of procedure claims. The method may further include calculating the percent of all procedures performed by the group's billing providers that were performed at the system using the same weights. The method may further include saving the group-system pairs and generating summary files for each system and each group. The summary files may include summary metrics for the system including the system's capture HHI sum of squared shares of system procedures. The summary files may further include summary metrics for the group including the group's capture HHI sum of squared shares of the group's procedures. The method can be repeated for all years of available claims.

The evaluation of procedure capture can yield multiple metrics, including the group-facility procedure capture metric, the group-system procedure capture metric, the facility-group procedure capture metric, the system-group procedure capture metric, the group-facility procedure capture score, the group-system procedure capture score, the facility-group procedure capture score, and the system-group procedure capture score. The group-facility procedure capture metric is the proportion of all facility claims performed at the facility that were performed by practitioners who billed under the group. The group-system procedure capture is the proportion of all facility claims performed at the system's facilities that were performed by practitioners who billed under the group. The facility-group procedure capture metric is the proportion of all facility claims performed by the group's billing practitioners that were performed at the facility. The system-group procedure capture metric is the proportion of all facility claims performed by the group's billing practitioners that were performed at the system's facilities. The group-facility procedure capture score is the sum of the squared group-facility billing capture metrics for the facility. The group-system procedure capture score is the sum of the squared group-system billing capture metrics for the system. The facility-group procedure capture score is the sum of the squared facility-group billing capture metrics for the group. The system-group procedure capture score is the sum of the squared system-group billing capture metrics for the group.

Figure 9:
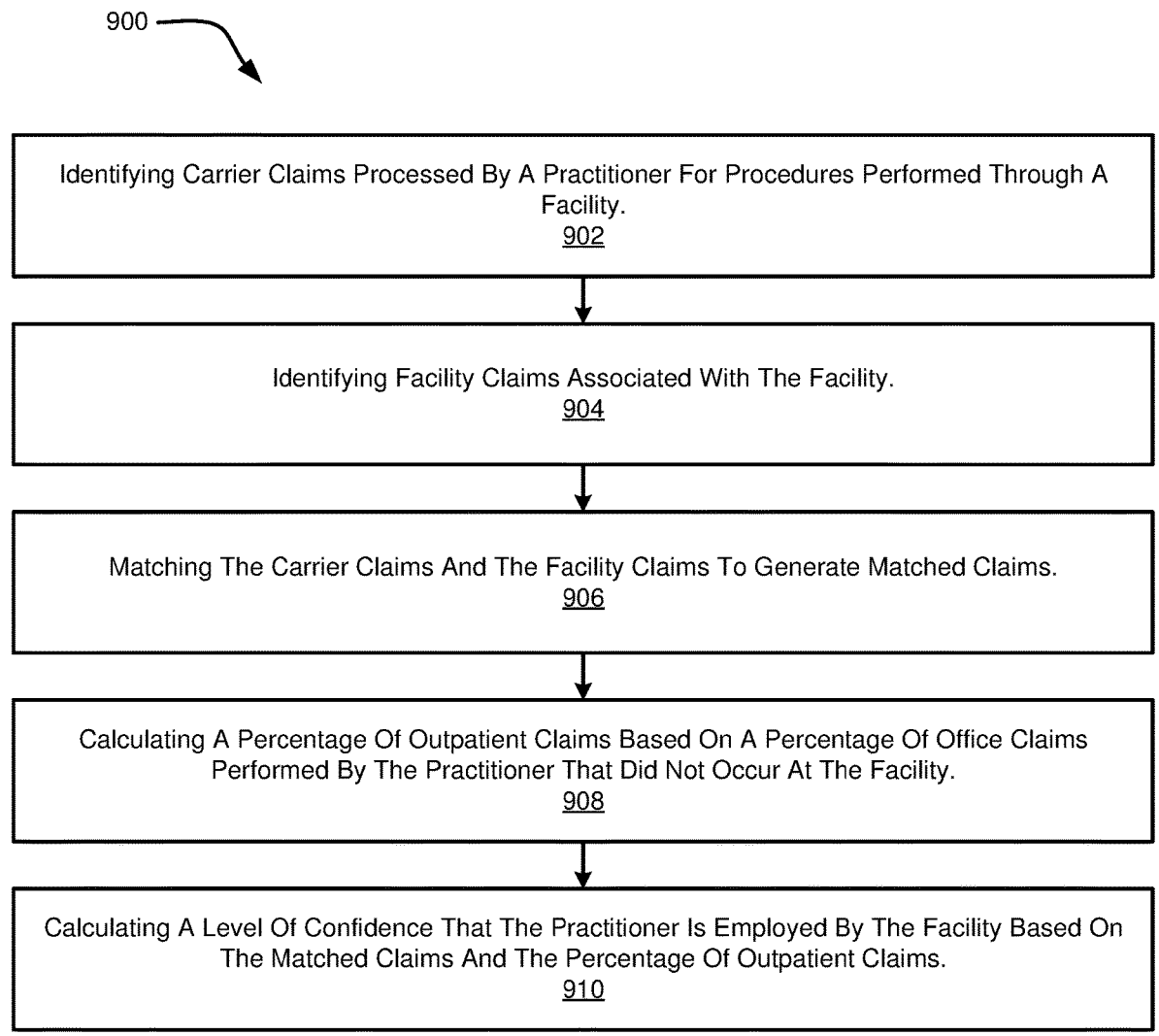
FIG. 9 is a schematic flow chart diagram of a method for determining whether a practitioner is likely employed by a facility.

FIG. 9 is a schematic flow chart diagram of a method 900 for determining whether a practitioner 102 is likely to be employed by a facility 110. The method 900 may be performed by one or more processors configurable to execute instructions stored in non-transitory computer readable storage media, or some other computing device or computing system.

The method 900 begins and a computing device identifies at 902 carrier claims processed by a practitioner for procedure performed through a facility. The method 900 continues and a computing device identifies at 904 facility claims associated with the facility. The method 900 continues and a computing device matches at 906 the carrier claims and the facility claims to generate matched claims. The method 900 continues and a computing device calculates at 908 a percentage of outpatient claims based on a percentage of office claims performed by the practitioner that did not occur at the facility. The method 900 continues and a computing device calculates at 910 a level of confidence that the practitioner is employed by the facility based on the matched claims and the percentage of outpatient claims.

In an embodiment, the carrier claims are matched to a facility and are not specifically matched to facility claims. This embodiment may be implemented in an instance where there are not available facility claims to match to the carrier claims. In an embodiment, both matching processes are implemented. In such an embodiment, facilities are merged with the carrier claims, and additionally, facility claims are merged with the carrier claims. This can be beneficial in an instance where some facility claims are available, and the accuracy of the final practitioner-facility employment 504 metric is enhanced by matching carrier claims to the facilities themselves.

Figure 10:
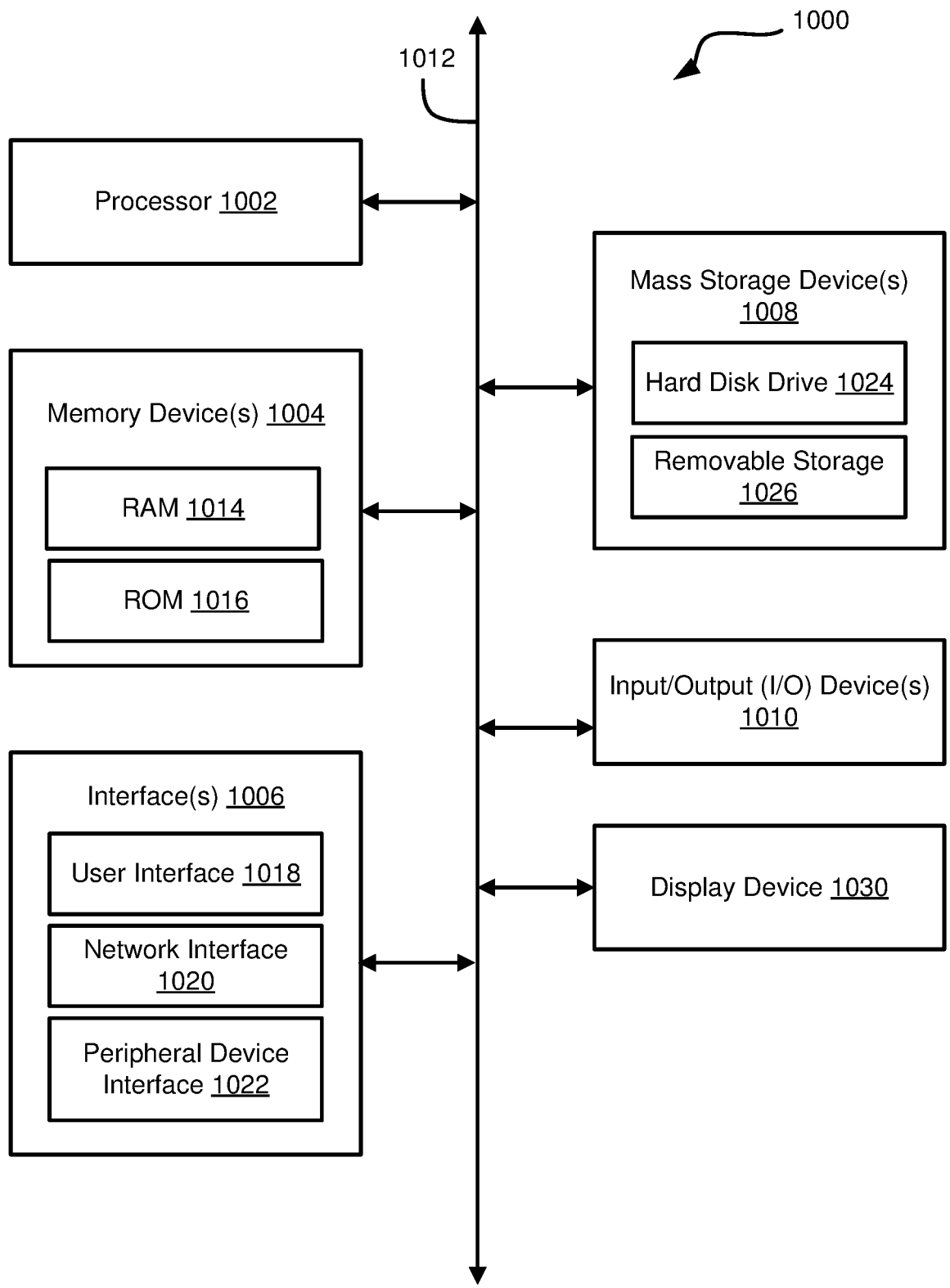
FIG. 10 is a schematic diagram illustrating components of an example computing device.

Referring now to FIG. 10, a block diagram of an example computing device 1000 is illustrated. Computing device 1000 may be used to perform various procedures, such as those discussed herein. Computing device 1000 can perform various monitoring functions as discussed herein, and can execute one or more application programs, such as the application programs or functionality described herein. Computing device 1000 can be any of a wide variety of computing devices, such as a desktop computer, in-dash computer, vehicle control system, a notebook computer, a server computer, a handheld computer, tablet computer and the like.

Computing device 1000 includes one or more processor(s) 1004, one or more memory device(s) 1004, one or more interface(s) 1006, one or more mass storage device(s) 1008, one or more Input/output (I/O) device(s) 1110, and a display device 1030 all of which are coupled to a bus 1012. Processor(s) 1004 include one or more processors or controllers that execute instructions stored in memory device(s) 1004 and/or mass storage device(s) 1008. Processor(s) 1004 may also include various types of computer-readable media, such as cache memory.

Memory device(s) 1004 include various computer-readable media, such as volatile memory (e.g., random access memory (RAM) 1014) and/or nonvolatile memory (e.g., read-only memory (ROM) 1016). Memory device(s) 1004 may also include rewritable ROM, such as Flash memory.

Mass storage device(s) 1008 include various computer readable media, such as magnetic tapes, magnetic disks, optical disks, solid-state memory (e.g., Flash memory), and so forth. As shown in FIG. 10, a particular mass storage device 1008 is a hard disk drive 1024. Various drives may also be included in mass storage device(s) 1008 to enable reading from and/or writing to the various computer readable media. Mass storage device(s) 1008 include removable media 1026 and/or non-removable media.

I/O device(s) 1010 include various devices that allow data and/or other information to be input to or retrieved from computing device 1000. Example I/O device(s) 1010 include cursor control devices, keyboards, keypads, microphones, monitors or other display devices, speakers, printers, network interface cards, modems, and the like.

Display device 1030 includes any type of device capable of displaying information to one or more users of computing device 1000. Examples of display device 1030 include a monitor, display terminal, video projection device, and the like.

Interface(s) 1006 include various interfaces that allow computing device 1000 to interact with other systems, devices, or computing environments. Example interface(s) 1006 may include any number of different network interfaces 1020, such as interfaces to local area networks (LANs), wide area networks (WANs), wireless networks, and the Internet. Other interface(s) include user interface 1018 and peripheral device interface 1022. The interface(s) 1006 may also include one or more user interface elements 1018. The interface(s) 1006 may also include one or more peripheral interfaces such as interfaces for printers, pointing devices (mice, track pad, or any suitable user interface now known to those of ordinary skill in the field, or later discovered), keyboards, and the like.

Bus 1012 allows processor(s) 1004, memory device(s) 1004, interface(s) 1006, mass storage device(s) 1008, and I/O device(s) 1010 to communicate with one another, as well as other devices or components coupled to bus 1012. Bus 1012 represents one or more of several types of bus structures, such as a system bus, PCI bus, IEEE bus, USB bus, and so forth.

For purposes of illustration, programs and other executable program components are shown herein as discrete blocks, such as block 202 for example, although it is understood that such programs and components may reside at various times in different storage components of computing device 1000 and are executed by processor(s) 1002. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

EXAMPLES

The following examples pertain to further embodiments.

Example 1 is a method for identifying and quantifying an employment relationship between a practitioner and a facility. The method includes matching a facility to a practitioner based on a facility identification associated with the facility and a billed claim submitted by the practitioner. The method includes calculating a percentage of claims submitted by the practitioner that were performed at the facility.

Example 2 is a method as in Example 1, wherein matching the facility to the practitioner includes merging based on one or more of: patient identification for the billed claim, service date of the billed claim, or Healthcare Common Procedure Coding (HCPC) code for the billed claim.

Example 3 is a method as in any of Examples 1-2, wherein matching the facility to the practitioner includes merging based on one or more of: patient identification for the billed claim, service date of the billed claim, or practitioner ID (National Provider Identifier) associated with the practitioner.

Example 4 is a method as in any of Examples 1-3, wherein matching the facility to the practitioner includes merging based on one or more of inpatient location in response to the billed claim occurring during a hospitalization matched to the facility.

Example 5 is a method as in any of Examples 1-4, wherein matching the facility to the practitioner includes merging based on one or more of: service date of the billed claim or a most common facility associated with the practitioner.

Example 6 is a method as in any of Examples 1-5, wherein matching the facility to the practitioner includes merging data based on a most common facility for the practitioner as determined based on an clinic ID for the most common facility.

Example 7 is a method as in any of Examples 1-6, wherein matching the facility to the practitioner includes merging data based on a service date of the billed claim or a most common facility of the practitioner.

Example 8 is a method as in any of Examples 1-7, wherein matching the facility to the practitioner includes merging data based on a service date of the billed claim or a most common facility of the practitioner within a two-week time period.

Example 9 is a method as in any of Examples 1-8, further comprising collapsing the matched practitioner and facility to a level of a healthcare group.

Example 10 is a method as in any of Examples 1-9, further comprising calculating a percent of claims processed by the healthcare group performed by practitioners employed by one or more facilities owned by the healthcare group.

Example 11 is a method. The method includes identifying carrier claims processed by a practitioner for procedures performed through a facility and matching the carrier claims to the facility to generate matched claims. The method includes calculating a percentage of outpatient claims based on a percentage of office claims performed by the practitioner that did not occur at the facility. The method includes calculating a level of confidence that the practitioner is employed by the facility based on the matched claims and the percentage of outpatient claims.

Example 12 is a method as in Example 11, wherein calculating the percentage of outpatient claims comprises collapsing the matched claims on an practitioner ID (National Provider Identifier) associated with the practitioner.

Example 13 is a method as in any of Examples 11-12, further comprising collapsing the matched claims to group level, wherein the facility is a healthcare facility associated with a group.

Example 14 is a method as in any of Examples 11-13, further comprising calculating a percentage of employment by calculating a percentage of practitioners associated with the group that are employed by a facility associated with the group.

Example 15 is a method as in any of Examples 11-14, wherein matching the carrier claims and the facility comprises matching based on: in a first matching iteration, a patient identification for a patient that received a procedure from the practitioner, a date of service for the procedure performed, and a procedure code for the procedure; in a second matching iteration, the patient identification, the date of service, and an practitioner ID (National Provider Identifier) associated with the practitioner; in a third matching iteration, an inpatient facility associated with a carrier claim if the carrier claim occurred during a hospitalization at the inpatient facility; in a fourth matching iteration, the date of service and a most common facility associated with the practitioner; and in a fifth matching iteration, the most common facility associated with the practitioner as determined based on an clinic ID (National Provider Identifier) in a carrier claim.

Example 16 is a method as in any of Examples 11-15, wherein matching the carrier claims and the facility further comprises matching based on: in a sixth matching iteration, the date of service and the most common facility associated with the practitioner; in a seventh matching iteration, the date of service and recent most common facility associated with the practitioner based on claims processed by the practitioner in a recent time period; in an eighth matching iteration, the date of service and the most common facility associated with the practitioner; in a ninth matching iteration, a most common provider associated with the practitioner using previously joined facilities; and in a tenth matching iteration, a facility most closely link to the clinic ID based on the carrier claim.

Example 17 is a method as in any of Examples 11-16, further comprising calculating a level of confidence that the practitioner is employed by the facility for each year there are available carrier claims, and aggregating the level of confidence for each year to calculate an aggregated level of confidence that the practitioner is employed by the facility.

Example 18 is a method as in any of Examples 11-17, wherein matching the carrier claims and the facility comprises matching based on one or more of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; or a facility most commonly linked to the clinic ID based on the carrier claims.

Example 19 is a method as in any of Examples 11-18, wherein matching the carrier claims and the facility comprises matching based on each of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; and a facility most commonly linked to the clinic ID based on the carrier claims.

Example 20 is a method as in any of Examples 11-19, further comprising determining that the practitioner is employed by the facility in response to determining that all carrier claims billed by the practitioner are matched to the facility.

Example 21 is one or more processors configurable to execute instructions stored in non-transitory computer readable storage media. The instructions include identifying carrier claims processed by a practitioner for procedures performed through a facility and matching the carrier claims and the facility to generate matched claims. The instructions include calculating a percentage of outpatient claims based on a percentage of office claims performed by the practitioner that did not occur at the facility. The instructions include calculating a level of confidence that the practitioner is employed by the facility based on the matched claims and the percentage of outpatient claims.

Example 22 is one or more processors as in Example 21, wherein the instructions are such that calculating the percentage of outpatient claims comprises collapsing the matched claims on an practitioner ID (National Provider Identifier) associated with the practitioner.

Example 23 is one or more processors as in any of Examples 21-22, wherein the instructions further comprise collapsing the matched claims to group level, wherein the facility is a healthcare facility associated with a group.

Example 24 is one or more processors as in any of Examples 21-23, wherein the instructions further comprise calculating a percentage of employment by calculating a percentage of practitioners associated with the group that are employed by a facility associated with the group.

Example 25 is one or more processors as in any of Examples 21-24, wherein the instructions are such that matching the carrier claims and the facility comprises matching based on: in a first matching iteration, a patient identification for a patient that received a procedure from the practitioner, a date of service for the procedure performed, and a procedure code for the procedure; in a second matching iteration, the patient identification, the date of service, and an practitioner ID (National Provider Identifier) associated with the practitioner; in a third matching iteration, an inpatient facility associated with a carrier claim if the carrier claim occurred during a hospitalization at the inpatient facility; in a fourth matching iteration, the date of service and a most common facility associated with the practitioner; and in a fifth matching iteration, the most common facility associated with the practitioner as determined based on an clinic ID (National Provider Identifier) in a carrier claim.

Example 26 is one or more processors as in any of Examples 21-25, wherein the instructions are such that matching the carrier claims and the facility further comprises matching based on: in a sixth matching iteration, the date of service and the most common facility associated with the practitioner; in a seventh matching iteration, the date of service and recent most common facility associated with the practitioner based on claims processed by the practitioner in a recent time period; in an eighth matching iteration, the date of service and the most common facility associated with the practitioner; in a ninth matching iteration, a most common provider associated with the practitioner using previously joined facilities; and in a tenth matching iteration, a facility most closely link to the clinic ID based on the carrier claim.

Example 27 is one or more processors as in any of Examples 21-26, wherein the instructions further comprise calculating a level of confidence that the practitioner is employed by the facility for each year there are available carrier claims to assess, and aggregating the level of confidence for each year to calculate an aggregated level of confidence that the practitioner is employed by the facility.

Example 28 is one or more processors as in any of Examples 21-27, wherein the instructions are such that matching the carrier claims and the facility comprises matching based on one or more of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; or a facility most commonly linked to the clinic ID based on the carrier claims.

Example 29 is one or more processors as in any of Examples 21-28, wherein the instructions are such that matching the carrier claims and the facility comprises matching based on each of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; and a facility most commonly linked to the clinic ID based on the carrier claims.

Example 30 is one or more processors as in any of Examples 21-29, wherein the instructions further comprise determining that the practitioner is employed by the facility in response to determining that all carrier claims billed by the practitioner are matched to the facility.

Example 31 is non-transitory computer readable storing media storing instructions to be implemented by one or more processors. The instructions include identifying carrier claims processed by a practitioner for procedures performed through a facility and matching the carrier claims and the facility to generate matched claims. The instructions include calculating a percentage of outpatient claims based on a percentage of office claims performed by the practitioner that did not occur at the facility. The instructions include calculating a level of confidence that the practitioner is employed by the facility based on the matched claims and the percentage of outpatient claims.

Example 32 is non-transitory computer readable storage media as in Example 31, wherein the instructions are such that calculating the percentage of outpatient claims comprises collapsing the matched claims on an practitioner ID (National Provider Identifier) associated with the practitioner.

Example 33 is non-transitory computer readable storage media as in any of Examples 31-22, wherein the instructions further comprise collapsing the matched claims to group level, wherein the facility is a healthcare facility associated with a group.

Example 34 is non-transitory computer readable storage media as in any of Examples 31-33, wherein the instructions further comprise calculating a percentage of employment by calculating a percentage of practitioners associated with the group that are employed by a facility associated with the group.

Example 35 is non-transitory computer readable storage media as in any of Examples 31-34, the instructions are such that matching the carrier claims and the facility comprises matching based on: in a first matching iteration, a patient identification for a patient that received a procedure from the practitioner, a date of service for the procedure performed, and a procedure code for the procedure; in a second matching iteration, the patient identification, the date of service, and an practitioner ID (National Provider Identifier) associated with the practitioner; in a third matching iteration, an inpatient facility associated with a carrier claim if the carrier claim occurred during a hospitalization at the inpatient facility; in a fourth matching iteration, the date of service and a most common facility associated with the practitioner; and in a fifth matching iteration, the most common facility associated with the practitioner as determined based on an clinic ID (National Provider Identifier) in a carrier claim.

Example 36 is non-transitory computer readable storage media as in any of Examples 31-35, wherein the instructions are such that matching the carrier claims and the facility further comprises matching based on: in a sixth matching iteration, the date of service and the most common facility associated with the practitioner; in a seventh matching iteration, the date of service and recent most common facility associated with the practitioner based on claims processed by the practitioner in a recent time period; in an eighth matching iteration, the date of service and the most common facility associated with the practitioner; in a ninth matching iteration, a most common provider associated with the practitioner using previously joined facilities; and in a tenth matching iteration, a facility most closely link to the clinic ID based on the carrier claim.

Example 37 is non-transitory computer readable storage media as in any of Examples 31-36, wherein the instructions further comprise calculating a level of confidence that the practitioner is employed by the facility for each year there are available carrier claims and available facility to assess, and aggregating the level of confidence for each year to calculate an aggregated level of confidence that the practitioner is employed by the facility.

Example 38 is non-transitory computer readable storage media as in any of Examples 31-37, wherein the instructions are such that matching the carrier claims and the facility comprises matching based on one or more of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; or a facility most commonly linked to the clinic ID based on the carrier claims.

Example 39 is non-transitory computer readable storage media as in any of Examples 31-38, wherein the instructions are such that matching the carrier claims and the facility comprises matching based on each of: a patient identification for a patient that received a procedure from the practitioner; a date of service for the procedure; a procedure code for the procedure; an practitioner ID (National Provider Identifier) associated with the practitioner; an inpatient facility associated with a carrier claim if the carrier claim occurred during a hospitalization at the inpatient facility; a most common facility that is most commonly associated with the practitioner; an clinic ID (National Provider Identifier) associated with the facility; and a facility most commonly linked to the clinic ID based on the carrier claims.

Example 40 is non-transitory computer readable storage media as in any of Examples 31-39, wherein the instructions further comprise determining that the practitioner is employed by the facility in response to determining that all carrier claims billed by the practitioner are matched to the facility.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method comprising:
aggregating data from a plurality of different data sources, wherein the data comprises raw claims data ingested from an external data source, wherein at least a portion of the raw claims data is encrypted, and wherein the raw claims data comprises carrier claims, wherein the carrier claims comprise data metrics that include calendar year, entity, practitioner identifier (ID), or facility identifier;
executing an electronic data security measure by de-encrypting the encrypted portion of the raw claims data;
generating an intermediary file from the de-encrypted raw claims data comprising a modeled version of the raw claims data, wherein the modeled version of the raw claims data is cleaned to eliminate superfluous data;
storing the intermediary file in a database;
partitioning the intermediary file based on one or more of the data metrics;
identifying a plurality of carrier claims processed by a practitioner for procedures performed at a facility, wherein the plurality of carrier claims is identified from within the partitioned version of the intermediary file that is stored in the database;
executing a database merge process to match the plurality of carrier claims to the facility to generate matched claims;
calculating a percentage of outpatient claims based on a percentage of office claims performed by the practitioner that did not occur at the facility; and
calculating a level of confidence that the practitioner is employed by the facility based on the matched claims and the percentage of outpatient claims;
wherein the database merge process comprises a plurality of steps, and wherein each of the plurality of steps comprises matching the plurality of carrier claims to the facility based on an identified data metric;
wherein calculating the level of confidence that the practitioner is employed by the facility reflects real-world associations between the practitioner and the facility based on real-world claims data; and
wherein the intermediary file decreases the amount of disc storage and/or Random Access Memory (RAM) needed to calculate the level of confidence that the practitioner is employed by the facility based on the real-world claims data.

2. The method of claim 1, wherein the raw claims data further comprises facility claims and the method further comprising identifying a plurality of facility claims within the partitioned version of the intermediary file that is stored on the database, wherein the plurality of facility claims is associated with the facility, and wherein matching the plurality of carrier claims to the facility comprises matching the plurality of carrier claims to the plurality of facility claims to generate the matched claims.

3. The method of claim 1, wherein calculating the percentage of outpatient claims comprises collapsing the matched claims on a practitioner ID associated with the practitioner.

4. The method of claim 1, further comprising collapsing the matched claims to group level, wherein the facility is a healthcare facility associated with a group.

5. The method of claim 4, further comprising calculating a percentage of employment by calculating a percentage of practitioners associated with the group that are employed by a facility associated with the group.

6. The method of claim 1, wherein the carrier claims further comprise patient identification, procedure, date of service, procedural code, inpatient facility, clinic identifier (ID), and wherein matching the plurality of carrier claims with the facility comprises matching based on:
in a first matching iteration, a patient identification for a patient that received a procedure from the practitioner, a date of service for the procedure performed, and a procedure code for the procedure;
in a second matching iteration, the patient identification, the date of service, and a practitioner ID (National Provider Identifier) associated with the practitioner;
in a third matching iteration, an inpatient facility associated with a carrier claim if the carrier claim occurred during a hospitalization at the inpatient facility;
in a fourth matching iteration, the date of service and a most common facility associated with the practitioner; and
in a fifth matching iteration, the most common facility associated with the practitioner as determined based on a clinic ID (National Provider Identifier) in a carrier claim.

7. The method of claim 6, wherein matching the plurality of carrier claims with the facility further comprises matching based on:
in a sixth matching iteration, the date of service and the most common facility associated with the practitioner;
in a seventh matching iteration, the date of service and recent most common facility associated with the practitioner based on claims processed by the practitioner in a recent time period;
in an eighth matching iteration, the date of service and the most common facility associated with the practitioner;
in a ninth matching iteration, a most common facility associated with the practitioner using previously joined facilities; and
in a tenth matching iteration, a facility most closely link to the clinic ID based on the carrier claim.

8. The method of claim 1, further comprising calculating a level of confidence that the practitioner is employed by the facility for each year there are available carrier claims and aggregating the level of confidence for each year to calculate an aggregated level of confidence that the practitioner is employed by the facility.

9. The method of claim 1, wherein the carrier claims further comprise patient identification, procedure, date of service, procedural code, inpatient facility, clinic identifier (ID), and wherein the plurality of steps for the database merge process comprises matching based on one or more of:
a patient identification for a patient that received a procedure from the practitioner;
a date of service for the procedure;
a procedure code for the procedure;
a practitioner ID (National Provider Identifier) associated with the practitioner;
an inpatient facility associated with a carrier claim if the carrier claim occurred during a hospitalization at the inpatient facility;
a most common facility that is most commonly associated with the practitioner;
a clinic ID (National Provider Identifier) associated with the facility; or a facility most commonly linked to the clinic ID based on the carrier claims.

10. The method of claim 1, wherein the carrier claims further comprise patient identification, procedure, date of service, procedural code, inpatient facility, clinic identifier (ID), and wherein the database merge process for matching the plurality of carrier claims with the facility comprises matching based on each of:
   a patient identification for a patient that received a procedure from the practitioner;
   a date of service for the procedure;
   a procedure code for the procedure;
   a practitioner ID (National Provider Identifier) associated with the practitioner;
   an inpatient facility associated with a carrier claim if the carrier claim occurred during a hospitalization at the inpatient facility;
   a most common facility that is most commonly associated with the practitioner;
   a clinic ID (National Provider Identifier) associated with the facility; and
   a facility most commonly linked to the clinic ID based on the carrier claims.

11. The method of claim 1, further comprising determining that the practitioner is employed by the facility in response to determining that all carrier claims billed by the practitioner are matched to the facility.

12. A system comprising one or more processors configured to execute instructions stored in non-transitory computer readable storage media, the instructions comprising:
   aggregating data from a plurality of different data sources, wherein the data comprises raw claims data ingested from an external data source, wherein at least a portion of the raw claims data is encrypted, and wherein the raw claims data comprises carrier claims, wherein the carrier claims comprise data metrics that include calendar year, entity, practitioner identifier (ID), or facility identifier;
   executing an electronic data security measure by de-encrypting the encrypted portion of the raw claims data;
   generating an intermediary file from the de-encrypted raw claims data comprising a modeled version of the raw claims data, wherein the modeled version of the raw claims data is cleaned to eliminate superfluous data;
   storing the intermediary file in a database;
   partitioning the intermediary file based on one or more of the data metrics;
   identifying a plurality of carrier claims processed by a practitioner for procedures performed at a facility, wherein the plurality of carrier claims is identified from within the partitioned version of the intermediary file that is stored in the database;
   executing a database merge process to match the plurality of carrier claims to the facility to generate matched claims;
   calculating a percentage of outpatient claims based on a percentage of office claims performed by the practitioner that did not occur at the facility; and
   calculating a level of confidence that the practitioner is employed by the facility based on the matched claims and the percentage of outpatient claims;
   wherein the database merge process comprises a plurality of steps, and wherein each of the plurality of steps comprises matching the plurality of carrier claims to the facility based on an identified data metric;
   wherein calculating the level of confidence that the practitioner is employed by the facility reflects real-world associations between the practitioner and the facility based on real-world claims data; and
   wherein the intermediary file decreases the amount of disc storage and/or Random Access Memory (RAM) needed to calculate the level of confidence that the practitioner is employed by the facility based on the real-world claims data.

13. The system of claim 12, wherein the raw claims data further comprises facility claims and wherein the instructions further comprise identifying a plurality of facility claims within the partitioned version of the intermediary file that is stored on the database, wherein the plurality of facility claims is associated with the facility, and wherein matching the plurality of carrier claims to the facility comprises matching the plurality of carrier claims to the plurality of facility claims to generate the matched claims.

14. The system of claim 12, wherein the instructions are such that calculating the percentage of outpatient claims comprises collapsing the matched claims on a practitioner ID (National Provider Identifier) associated with the practitioner.

15. The system of claim 12, wherein the instructions further comprise collapsing the matched claims to group level, wherein the facility is a healthcare facility associated with a group.

16. The system of claim 15, wherein the instructions further comprise calculating a percentage of employment by calculating a percentage of practitioners associated with the group that are employed by a facility associated with the group.

17. The system of claim 12, wherein the carrier claims further comprise patient identification, procedure, date of service, procedural code, inpatient facility, clinic identifier (ID), and wherein the instructions are such that matching the plurality of carrier claims to the facility comprises matching based on:
   in a first matching iteration, a patient identification for a patient that received a procedure from the practitioner, a date of service for the procedure performed, and a procedure code for the procedure;
   in a second matching iteration, the patient identification, the date of service, and a practitioner ID (National Provider Identifier) associated with the practitioner;
   in a third matching iteration, an inpatient facility associated with a carrier claim if the carrier claim occurred during a hospitalization at the inpatient facility;
   in a fourth matching iteration, the date of service and a most common facility associated with the practitioner; and
   in a fifth matching iteration, the most common facility associated with the practitioner as determined based on a clinic ID (National Provider Identifier) in a carrier claim.

18. The system of claim 17, wherein the instructions are such that matching the plurality of carrier claims to the facility further comprises matching based on:
   in a sixth matching iteration, the date of service and the most common facility associated with the practitioner;
   in a seventh matching iteration, the date of service and recent most common facility associated with the practitioner based on claims processed by the practitioner in a recent time period;
   in an eighth matching iteration, the date of service and the most common facility associated with the practitioner;

in a ninth matching iteration, a most common provider associated with the practitioner using previously joined facilities; and in a tenth matching iteration, a facility most closely link to the clinic ID based on the carrier claim.

19. The system of claim 12, wherein the instructions further comprise:

calculating a level of confidence that the practitioner is employed by the facility for each year there are available carrier claims to assess; and aggregating the level of confidence for each year to calculate an aggregated level of confidence that the practitioner is employed by the facility.

20. The system of claim 12, wherein the carrier claims further comprise patient identification, procedure, date of service, procedural code, inpatient facility, clinic identifier (ID), and wherein the instructions are such that the plurality of steps for the database merge process comprises matching based on one or more of:

a patient identification for a patient that received a procedure from the practitioner;

a date of service for the procedure;

a procedure code for the procedure;

a practitioner ID (National Provider Identifier) associated with the practitioner;

an inpatient facility associated with a carrier claim if the carrier claim occurred during a hospitalization at the inpatient facility;

a most common facility that is most commonly associated with the practitioner;

a clinic ID (National Provider Identifier) associated with the facility; or a facility most commonly linked to the clinic ID based on the carrier claims.

21. The system of claim 12, wherein the carrier claims further comprise patient identification, procedure, date of service, procedural code, inpatient facility, clinic identifier (ID), and wherein the instructions are such that the database merge process for matching the plurality of carrier claims to the facility comprises matching based on each of:

a patient identification for a patient that received a procedure from the practitioner;

a date of service for the procedure;

a procedure code for the procedure;

a practitioner ID (National Provider Identifier) associated with the practitioner;

an inpatient facility associated with a carrier claim if the carrier claim occurred during a hospitalization at the inpatient facility;

a most common facility that is most commonly associated with the practitioner;

a clinic ID (National Provider Identifier) associated with the facility; and a facility most commonly linked to the clinic ID based on the carrier claims.

22. The system of claim 12, wherein the instructions further comprise determining that the practitioner is employed by the facility in response to determining that all carrier claims billed by the practitioner are matched to the facility.

23. Non-transitory computer readable storage media storing instructions to be implemented by one or more processors, the instructions comprising:

aggregating data from a plurality of different data sources, wherein the data comprises raw claims data ingested from an external data source, wherein at least a portion of the raw claims data is encrypted, and wherein the raw claims data comprises carrier claims, wherein the carrier claims comprise data metrics that include calendar year, entity, practitioner identifier (ID), or facility identifier;

executing an electronic data security measure by de-encrypting the encrypted portion of the raw claims data;

generating an intermediary file from the de-encrypted raw claims data comprising a modeled version of the raw claims data, wherein the modeled version of the raw claims data is cleaned to eliminate superfluous data;

storing the intermediary file in a database;

partitioning the intermediary file based on one or more of the data metrics;

identifying a plurality of carrier claims processed by a practitioner for procedures performed at a facility, wherein the plurality of carrier claims is identified from within the partitioned version of the intermediary file that is stored in the database;

executing a database merge process to match the plurality of carrier claims to the facility to generate matched claims;

calculating a percentage of outpatient claims based on a percentage of office claims performed by the practitioner that did not occur at the facility; and calculating a level of confidence that the practitioner is employed by the facility based on the matched claims and the percentage of outpatient claims;

wherein the database merge process comprises a plurality of steps, and wherein each of the plurality of steps comprises matching the plurality of carrier claims to the facility based on an identified data metric;

wherein calculating the level of confidence that the practitioner is employed by the facility reflects real-world associations between the practitioner and the facility based on real-world claims data; and wherein the intermediary file decreases the amount of disc storage and/or Random Access Memory (RAM) needed to calculate the level of confidence that the practitioner is employed by the facility based on the real-world claims data.

24. The non-transitory computer readable storage media of claim 23, wherein the raw claims data further comprises facility claims and wherein the instructions further comprise identifying a plurality of facility claims within the partitioned version of the intermediary file that is stored on the database, wherein the plurality of facility claims is associated with the facility, and wherein matching the plurality of carrier claims to the facility comprises matching the plurality of carrier claims to the plurality of facility claims to generate the matched claims.

25. The non-transitory computer readable storage media of claim 23, wherein the instructions are such that calculating the percentage of outpatient claims comprises collapsing the matched claims on a practitioner ID (National Provider Identifier) associated with the practitioner.

26. The non-transitory computer readable storage media of claim 23, wherein the instructions further comprise collapsing the matched claims to group level, wherein the facility is a healthcare facility associated with a group.

27. The non-transitory computer readable storage media of claim 26, wherein the instructions further comprise calculating a percentage of employment by calculating a percentage of practitioners associated with the group that are employed by a facility associated with the group.

28. The non-transitory computer readable storage media of claim 23, wherein the carrier claims further comprise patient identification, procedure, date of service, procedural code, inpatient facility, clinic identifier (ID), and wherein the instructions are such that matching the plurality of carrier claims to the facility comprises matching based on:
- in a first matching iteration, a patient identification for a patient that received a procedure from the practitioner, a date of service for the procedure performed, and a procedure code for the procedure;
- in a second matching iteration, the patient identification, the date of service, and a practitioner ID (National Provider Identifier) associated with the practitioner;
- in a third matching iteration, an inpatient facility associated with a carrier claim if the carrier claim occurred during a hospitalization at the inpatient facility;
- in a fourth matching iteration, the date of service and a most common facility associated with the practitioner; and
- in a fifth matching iteration, the most common facility associated with the practitioner as determined based on a clinic ID (National Provider Identifier) in a carrier claim.

29. The non-transitory computer readable storage media of claim 28, wherein the instructions are such that matching the plurality of carrier claims to the facility further comprises matching based on:
- in a sixth matching iteration, the date of service and the most common facility associated with the practitioner;
- in a seventh matching iteration, the date of service and recent most common facility associated with the practitioner based on claims processed by the practitioner in a recent time period;
- in an eighth matching iteration, the date of service and the most common facility associated with the practitioner;
- in a ninth matching iteration, a most common provider associated with the practitioner using previously joined facilities; and
- in a tenth matching iteration, a facility most closely link to the clinic ID based on the carrier claim.

30. The non-transitory computer readable storage media of claim 23, wherein the instructions further comprise calculating a level of confidence that the practitioner is employed by the facility for each year there are available carrier claims to assess, and aggregating the level of confidence for each year to calculate an aggregated level of confidence that the practitioner is employed by the facility.

31. The non-transitory computer readable storage media of claim 23, wherein the carrier claims further comprise patient identification, procedure, date of service, procedural code, inpatient facility, clinic identifier (ID), and wherein the instructions are such that the plurality of steps for the database merge process comprises matching based on one or more of:
- a patient identification for a patient that received a procedure from the practitioner;
- a date of service for the procedure;
- a procedure code for the procedure;
- a practitioner ID (National Provider Identifier) associated with the practitioner;
- an inpatient facility associated with a carrier claim if the carrier claim occurred during a hospitalization at the inpatient facility;
- a most common facility that is most commonly associated with the practitioner;
- a clinic ID (National Provider Identifier) associated with the facility; or
- a facility most commonly linked to the clinic ID based on the carrier claims.

32. The non-transitory computer readable storage media of claim 23, wherein the carrier claims further comprise patient identification, procedure, date of service, procedural code, inpatient facility, clinic identifier (ID), and wherein the instructions are such that the database merge process for matching the plurality of carrier claims to the facility comprises matching based on each of:
- a patient identification for a patient that received a procedure from the practitioner;
- a date of service for the procedure;
- a procedure code for the procedure;
- a practitioner ID (National Provider Identifier) associated with the practitioner;
- an inpatient facility associated with a carrier claim if the carrier claim occurred during a hospitalization at the inpatient facility;
- a most common facility that is most commonly associated with the practitioner;
- a clinic ID (National Provider Identifier) associated with the facility; and
- a facility most commonly linked to the clinic ID based on the carrier claims.

33. The non-transitory computer readable storage media of claim 23, wherein the instructions further comprise determining that the practitioner is employed by the facility in response to determining that all carrier claims billed by the practitioner are matched to the facility.

* * * * *